(12) United States Patent
Gressel et al.

(10) Patent No.: US 9,938,492 B2
(45) Date of Patent: Apr. 10, 2018

(54) PHOTOBIOREACTOR FOR ENCLOSED HORIZONTAL CULTIVATION OF MICROALGAE

(71) Applicants: Jonathan Gressel, Washington, DC (US); Mordechai Granot, Washington, DC (US)

(72) Inventors: Jonathan Gressel, Washington, DC (US); Mordechai Granot, Washington, DC (US)

( * ) Notice: Subject to any disclaimer, the term of this patent is extended or adjusted under 35 U.S.C. 154(b) by 0 days.

(21) Appl. No.: 14/436,891

(22) PCT Filed: Oct. 22, 2013

(86) PCT No.: PCT/IB2013/059522
§ 371 (c)(1),
(2) Date: Apr. 18, 2015

(87) PCT Pub. No.: WO2014/064602
PCT Pub. Date: May 1, 2014

(65) Prior Publication Data
US 2015/0275161 A1    Oct. 1, 2015

(51) Int. Cl.
| | |
|---|---|
| *C12M 1/00* | (2006.01) |
| *C12M 1/04* | (2006.01) |
| *C12M 1/09* | (2006.01) |
| *C12M 3/06* | (2006.01) |
| *C12M 1/02* | (2006.01) |
| *A01G 1/00* | (2006.01) |
| *A01G 33/00* | (2006.01) |
| *C12M 1/12* | (2006.01) |

(52) U.S. Cl.
CPC ............ *C12M 21/02* (2013.01); *A01G 1/001* (2013.01); *A01G 33/00* (2013.01); *C12M 23/06* (2013.01); *C12M 23/14* (2013.01); *C12M 23/24* (2013.01); *C12M 23/26* (2013.01); *C12M 23/56* (2013.01); *C12M 27/16* (2013.01); *C12M 41/22* (2013.01); *Y02P 60/247* (2015.11)

(58) Field of Classification Search
None
See application file for complete search history.

(56) References Cited

U.S. PATENT DOCUMENTS

| | | | |
|---|---|---|---|
| 5,711,888 | A | 1/1998 | Trampler et al. |
| 2004/0242746 | A1 | 12/2004 | Freedman et al. |
| 2009/0130706 | A1 | 5/2009 | Berzin et al. |

FOREIGN PATENT DOCUMENTS

| | | |
|---|---|---|
| WO | 2011/017171 A1 | 2/2011 |
| WO | 2012/110256 A1 | 8/2012 |

OTHER PUBLICATIONS

Kang, KS; et al., Effects of Combined Mechanical Stimulation on the Proliferation and Differentiation of Pre-Osleoblasts. Experimental' and Molecular Medicine. Jun. 2011.
Les, DH; et al., Phylogeny and Systematics of Lemnaceae. The Duckweed Family. Systematic Botany. 2002, vol. 27, No. 2.

*Primary Examiner* — Thane Underdahl
(74) *Attorney, Agent, or Firm* — Allen D. Hertz, P.A.; Allen D. Hertz

(57) ABSTRACT

A photobioreactor comprising a sealed, covered plastic sheeting coated with a thin layer of a highly dense culture of photoautotrophic single celled organism. Carbon dioxide is exchanged from a gas space above the culture through attendant mixing by subtending wave motion. The photobioreactor provides a substantial improvement in processing costs in growth media sterilization as well as reduced expenses related to energy and raw materials, especially carbon dioxide. Capital expenses are reduced by eliminating the need for sparging and compressors for suspending cells and mixing carbon dioxide.

28 Claims, 18 Drawing Sheets

Thin Layer Photo Bio Reactor (TLBPR) System Component and Functions

| Tag Pt. | Sub-system | Type of Device Controlled | Function | Comments |
|---|---|---|---|---|
| A | Algae Feed | Solenoid Valve | Control ingress of fertilizer concentrate into algae mixer | |
| B | Algae Feed | Solenoid Valve | Control ingress of water into algae mixer | |
| C | Algae Feed | Power ON/Off | Activate UV Sterilizer | Sterilize water and fertilizer |
| D | Algae Feed | UV in sterilization chamber ON detector | Indicate operation of UV sterilizer | |
| E | Algae Feed | Solenoid Valve | Control ingress of material concentrate into algae mixer algae bio-reactor | |
| F | Algae Feed | Solenoid Valve | Control ingress of sterilized water and fertilizer into algae mixer | |
| G | Algae Feed | Solenoid Valve | Control ingress of sterilized water/fertilizer and algae feed into Bladder | |
| H | $CO_2$ | Solenoid Valve | Control ingress of $CO_2$ into Bladder | Provide the $CO_2$ necessary for algae growth. Acidic pH level detected by L will open H (H=0). |
| I | Bladder | Mini or Micro Wave Generator— electrically driven eccentric vibrator | ON/OFF of slurry agitation | Agitate slurry in Bladder |
| J | Bladder | Temperature sensitive thermocouple | Indication of slurry temperature | Maintain stable temperature conditions of growth process in Bladder |
| K | Bladder | Coolant pump | Power ON/OFF | Inject cooler water into basin to maintain optimal growth temperature |
| L | Bladder | pH sensor | pH level | Indicate when batch growth is complete. Provides indication for acidic slurry caused by too much $CO_2$ |
| M | Algae Harvesting | Solenoid valve | Allow slurry sampling by sampling pump | Part of subsystem that indicated maturity of slurry |
| M' | Algae Harvesting | Slurry sampling pump | Power ON/OFF | Activation of M and M' facilitates ingress of slurry into dual wavelength photometer. Activation of M and M' cannot be done simultaneously with P and P'. |
| N | Algae Harvesting | Dual Wavelength Photometer Output | Indicate maturity of slurry for harvesting | |
| P | Algae Harvesting | Solenoid valve | Allow pumping of harvested algae | |
| P' | Algae Harvesting | Slurry Harvesting pump | Power ON/OFF | Activation of P and P' cannot be done simultaneously with M and M'. |
| Q | $CO_2$ Purging | Solenoid valve | Allow purge of air and build up of CO2 pressure in Bladder | Open before ingress of slurry into Bladder |

Figure 2B

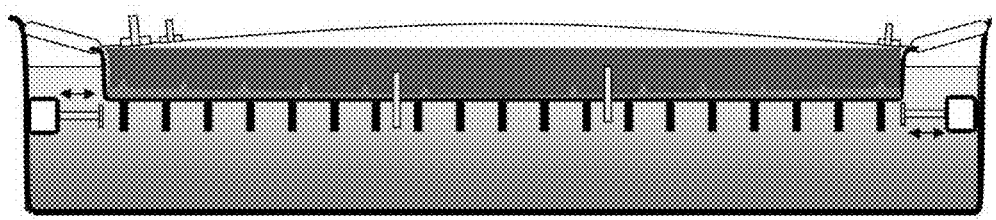

Longitudinal agitation with fins adhered to the ventral portion of the bioreactor. The fin ridges are set parallel to the longest dimension of the bioreactor.

Figure 4

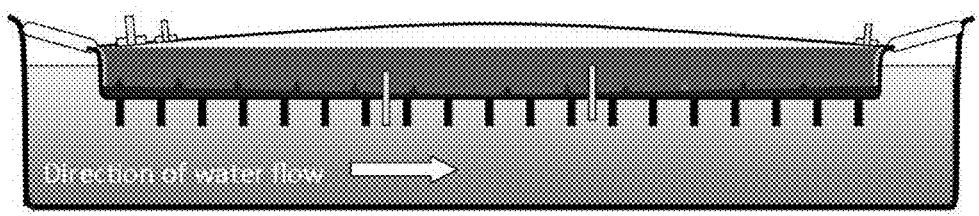

Longitudinal agitation with fins adhered to the ventral portion of the bioreactor. The fin ridges are set parallel to the longest dimension of the bioreactor. Waves generated by water flow are transferred mechanically through the fins to the algae slurry.

Figure 5

A Piezoelectric wire mesh submerged in the TLPBR sump, and adhered to it, replaces the discrete transducers. The mesh matrix of perpendicular piezoelectric wires allows programming unique agitation sequences for each type of algae slurry.

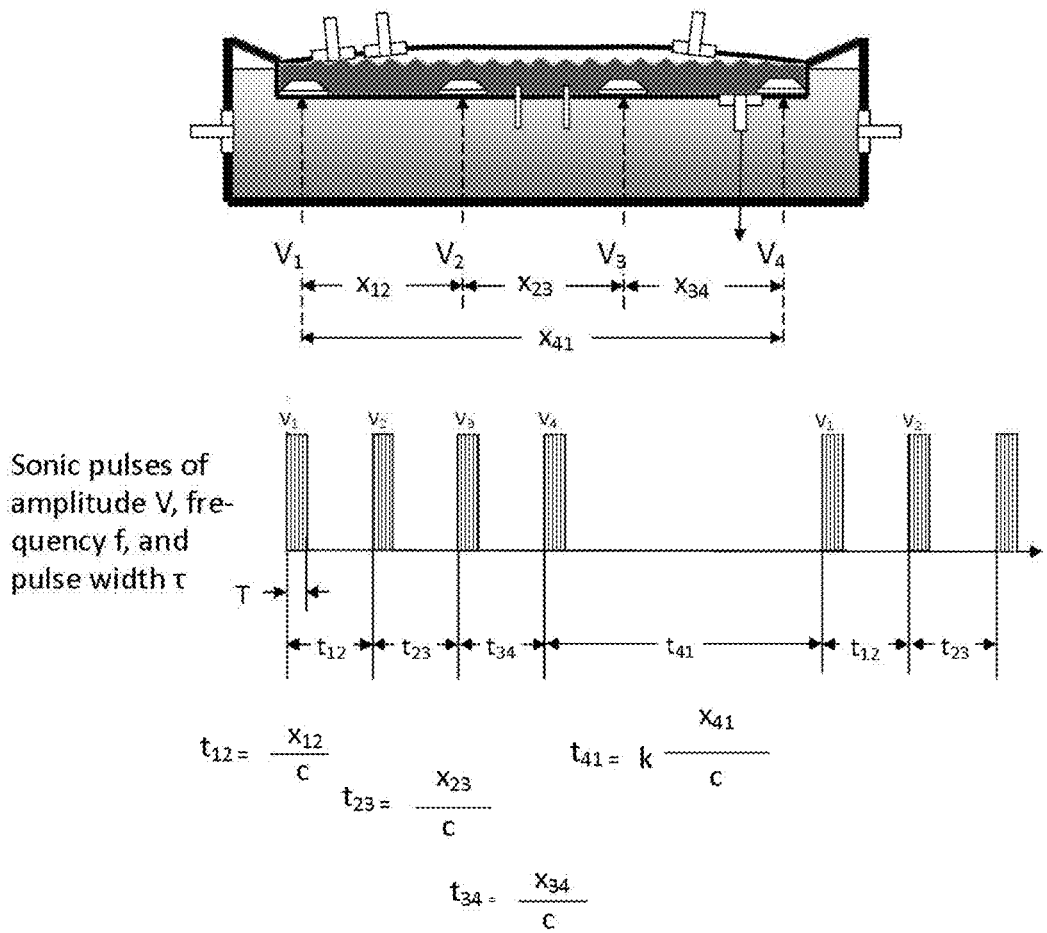

Matrix Array Staggered Pulse

Sonic pulses of amplitude V, frequency f, and pulse width τ

$$t_{12} = \frac{x_{12}}{c}$$
$$t_{23} = \frac{x_{23}}{c}$$
$$t_{34} = \frac{x_{34}}{c}$$
$$t_{41} = k\frac{x_{41}}{c}$$

Where
- t is the time, in seconds for the wave front to propagate from a transducer to the one adjacent to it.
- c is the speed of sound in $^m/_{sec}$ in the slurry medium, and
- x is the distance between transducers in meters Exciting the transducers in a sequentially timed manner will intensify the wave as it propogates past it. Therefore, the back wave between tranducers 4 and 1 should be allowed to time dampen its amplitude, hence the factor k> 1 in $t_{41}$.

Figure 6B

Synchronized excitation from lateral and ventral sides of the TLPBR provides other excitation options for denser algae slurries and assist their harvesting.

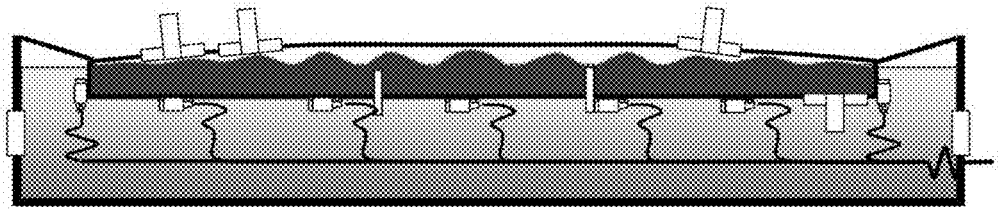

Three dimensional lattice Excitation by Eccentric Vibrators

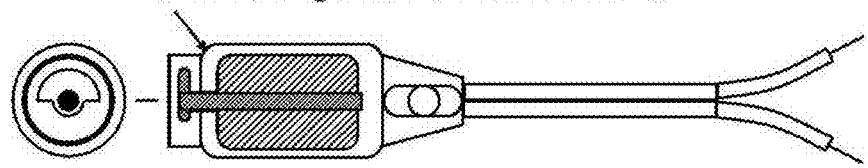

Eccentric mini-vibrators, arranged in a matrix on the ventral side of the sump provide low energy excitation options.

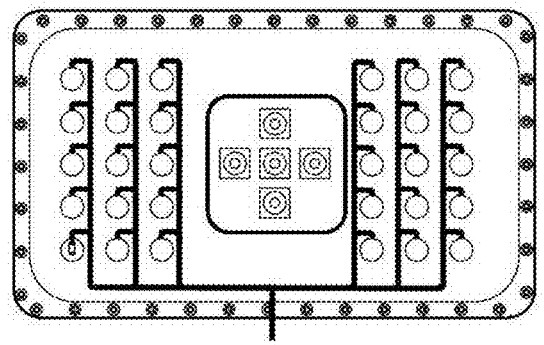

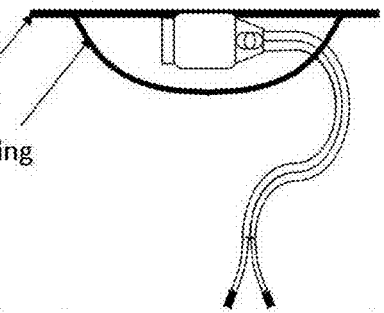

TLPBR Bladder
— Ventral Side

Conformal Potting

Conformal Potting (e.g. silicone based RTV, EP 930 V or equivalent)
1. provides adhesion of the eccentric vibrator to the Dorsal Bladder outer surface,
2. water proofing from the coolant, and,
3. outer layer of potting is formed and semi rigid and serves as a vibration reflector.

Figure 8A

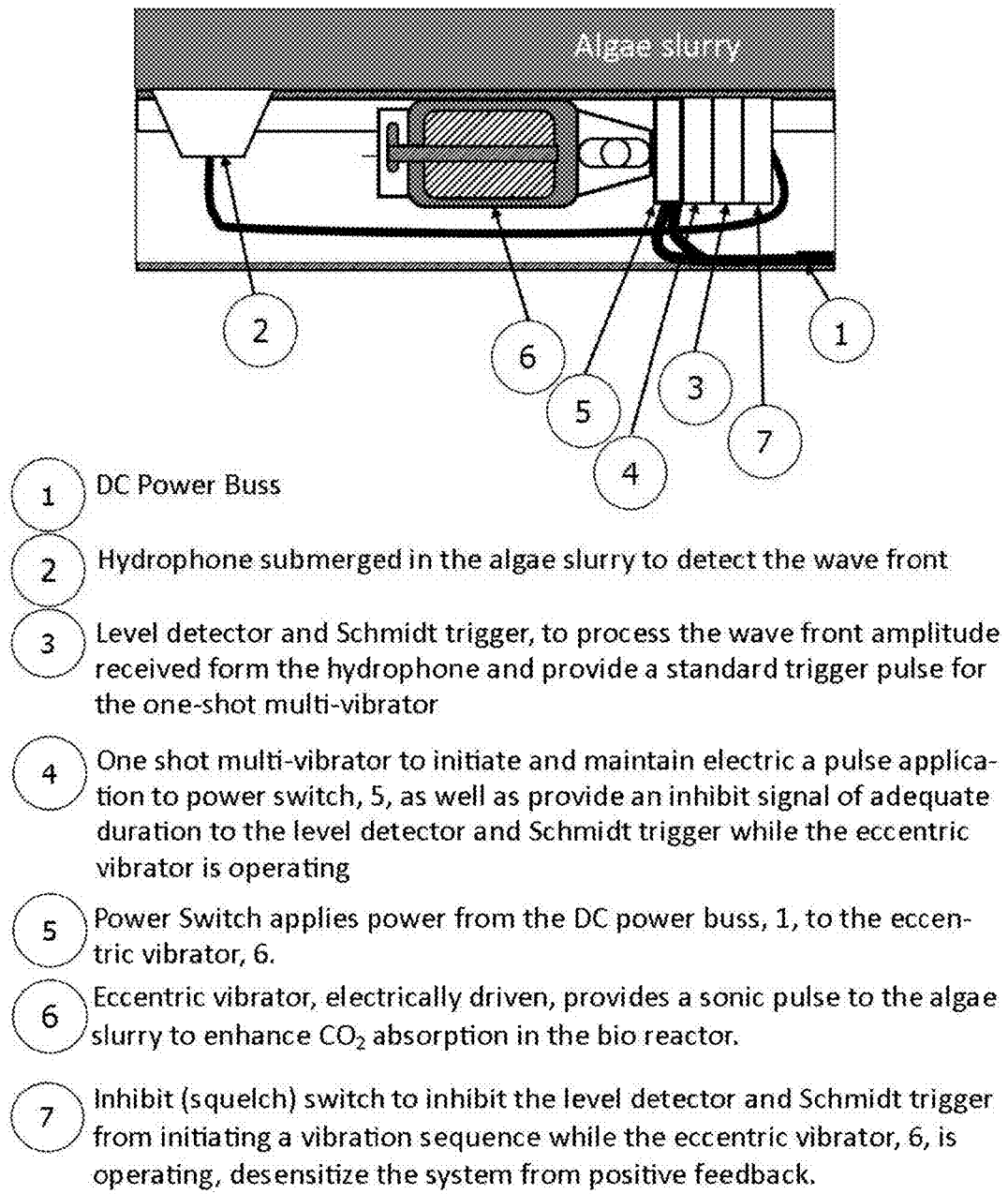

1. DC Power Buss

2. Hydrophone submerged in the algae slurry to detect the wave front

3. Level detector and Schmidt trigger, to process the wave front amplitude received form the hydrophone and provide a standard trigger pulse for the one-shot multi-vibrator 4. One shot multi-vibrator to initiate and maintain electric a pulse application to power switch, 5, as well as provide an inhibit signal of adequate duration to the level detector and Schmidt trigger while the eccentric vibrator is operating 5. Power Switch applies power from the DC power buss, 1, to the eccentric vibrator, 6.

6. Eccentric vibrator, electrically driven, provides a sonic pulse to the algae slurry to enhance $CO_2$ absorption in the bio reactor.

7. Inhibit (squelch) switch to inhibit the level detector and Schmidt trigger from initiating a vibration sequence while the eccentric vibrator, 6, is operating, desensitize the system from positive feedback.

Figure 8D

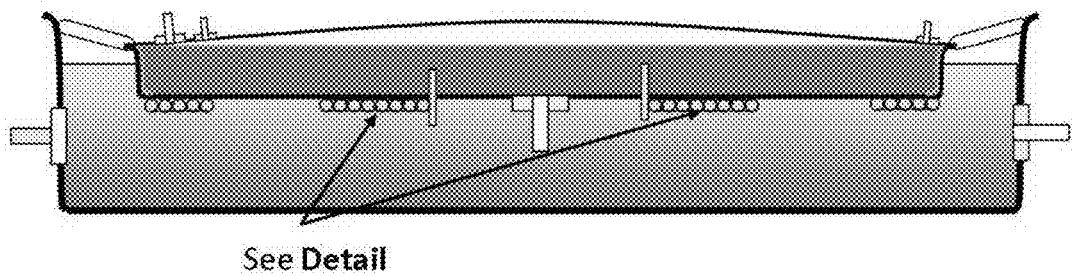

See Detail

Detail — Typical Bubble Strip Cross Section

Bubbled plastic sheeting strips are adhered to the ventral side of the photobioreactor. As the strips and the photobioreactor are immersed in the cooling water, the buoyancy forces of these strips impart the ventral side counteract the natural sag of the bioreactor basin.

The strips are located so as not to impede cooling, as well as facilitate harvesting by gravity by allowing some sag.

Figure 9

High Capacity Slow Flow Continuous Photo Bio Reactor

PHOTOBIOREACTOR FOR ENCLOSED HORIZONTAL CULTIVATION OF MICROALGAE

CROSS REFERENCE TO RELATED APPLICATIONS

This is a National Stage Application claiming the benefit of International Application Number PCT/IB2013/059522 filed on 22 Oct. 2013, which claims the benefit of United Stated Provisional Patent Application Ser. No. 61/795,661, filed on 22 Oct. 2012, both of which are incorporated herein by reference in their entireties.

FIELD OF THE INVENTION

This invention pertains to a novel closed system photobioreactor comprising plastic sheeting, sealed to form a container or tubular flat sleeve, coated with a thin layer of a highly dense culture of photoautotrophic single celled organism. Carbon dioxide is exchanged from the sealed, enclosed gas space above the horizontal culture through attendant mixing by subtending wave motion. The invention provides a substantial improvement in processing costs, in growth media sterilization, as well as reduced expenses related to energy and raw materials, especially carbon dioxide. Capital expenses are reduced by eliminating the need for sparging and compressors used for suspending cells and mixing carbon dioxide.

BACKGROUND OF THE INVENTION

Microalgae (broadly defined herein to include photosynthetic single celled eukaryotic algae and cyanobacteria) have a very high growth potential; more than ten times the productivity per unit area compared to terrestrial crops. Microalgae are potentially appropriate raw materials for producing low cost biofuels, animal feeds, and other products. Various impediments have prevented achieving this potential; the biological impediments of using undomesticated organisms are being overcome by genetic engineering of the microalgae (Gressel 2013). The impediment of the high cost of algal harvesting (dewatering) by high-speed (energy intensive) centrifugation has been overcome by a novel flocculation technology that is dependent on cultivating dense cultures of the microalgae (US2011/081706). The major remaining impediments are in cultivation; both in the expense of the structures used, and the high costs of running them. Open raceway ponds and their derivatives are inexpensive to construct, but must have a depth of at least 40 cm to allow adequate mixing and dissolution of bubbled (sparged) carbon dioxide. Even then, a considerable amount of carbon dioxide is lost to the atmosphere. The algae must be kept relatively dilute to allow light penetration, and even then all photons are typically absorbed in the upper 5-10 cm, and the material below respires photosynthate, decreasing yield from its potential. There is a high cost in sterilizing the large volumes of water used, in the compressors needed for bubbling, in the paddle wheels for mixing, and for the unused carbon dioxide lost. Cooling of open raceways is inexpensive in dry climates, i.e. is evaporative, requiring replacement with fresh water, even with marine algae to prevent over salinization. Open systems are easily contaminated by other unwanted species, including other algae, microbes, and algae-eating protozoan and metazoan herbivores, and thus various closed systems have been designed, but cooling is especially expensive for closed systems, because the deep water adsorbs infrared radiation that causes heating, which cannot be dissipated by evaporative cooling.

A generic diagram of such a closed bioreactor is shown in FIG. 1, and how it fits in a general cultivation system is outlined in FIG. 2 A, B, C. This design differs substantially from the many designs proposed for photobioreactors (see Table 1 below), as the algae herein are cultivated in a concentrated thin layer, which together with the use of near shear wave motion, renders sparging as unnecessary.

TABLE 1

Designs of sun-lit photobioreactors with insufficient light penetration
to most cells in dense culture and inefficient carbon-dioxide mixing

| Photobioreactor configuration | Optical path thickness (mm) | Carbon dioxide supply | Comments | Reference[c] |
|---|---|---|---|---|
| Vertical[b] Airlift type | | | | |
| Concentric tube Bubble-column in airlift | 130 | sparging | | Contreras et al. (1998) Merchuk et al. (2000) |
| Tubular | | | | |
| Tubular | 50-600 | Mixing bubbles | | PCT/US2009/056747 |
| Bags Submerged in water | Not stated | Tyvek tube spargers | | PCT/US2009/046782 |
| Helical tubular | 30 | Sparging in airlift | | Hall et al. (2003) |
| Parallel tubular | | | | Olaizola (2000) |
| Tubes in manifold | 25-50 | Bubbling | Mixing air with/without $CO_2$ | US 2011/0104790 |
| Hanging bag | 100-200 | Air flow | | Moheimani 2012 |
| Plates | | | | |
| Parallel plates | ndg | Sparging | Tiltable | US 2011/051507 |
| Parallel rigid plates | 10-1000 | Sparging | | PCT/US2011/040366 |
| Parallel plates | 100-250 | Sparging | Floating | DE 102008/022 676 |
| Flexible parallel plates | 50-60 | Bubbling | Internal heat exchanger | WO 2005/006838 |
| Flexible Parallel plates | June 25 | Jets | Squeeze mixing | WO 2009155032 |
| Flat plate | 100 | Sparging | | Cheng-Wu et al. (2001) |
| Flat plate | | | | PCT/US2011/040366 |

TABLE 1-continued

Designs of sun-lit photobioreactors with insufficient light penetration
to most cells in dense culture and inefficient carbon-dioxide mixing

| Photobioreactor configuration | Optical path thickness (mm) | Carbon dioxide supply | Comments | Reference[c] |
|---|---|---|---|---|
| Variable flat plate floating | 62 | Sparging | In parallel clusters | US 2011/0281340 |
| Thin layer flat plate | 10 | Sparging | Experimental | Xue 2011 |
| Variable flat plate cluster | 100-20 in cluster | | | US 2010/0028976 |
| Flat plate | 15-25 | Bubbles | | Zhang et al. (2002) |

On solids

| Hollow trabeculae | ndg | Sparging | Pivoting | US 2011/0306121 |
|---|---|---|---|---|
| Various | 2-7 | Sparging | Supplementary lighting | EP 1 995 304 |
| Fabric sheets | Thin layer on fibers | Diffusion from air | | WO 2011/138477 |
| Immobilized fibers | Thin layer on non woven fibers | In flow liquid | | U.S. Pat. No. 7,745,201 |

Inclined[b]

| Inclined tubular | 100 | Sparger | With mixing baffles | US 2005/026053 |
|---|---|---|---|---|
| Inclined tubular | 38-125 | Sparger | Static mixer in airlift | Ugwu et al. (2003) |
| Tubular -airlift | 300-1000 | Sparger | | PCT/US2005/025367 |
| Tubular | 50-1000 | "Introduced" | With cleaning vanes | Appl. GB 2,330,589 |
| Open - thin layer | 5-18 | Sparging in recirculation | Down hill flow | U.S. Pat. No. 5,981,271 |
| Cascade of flat plates | 20 | Sparging in recirculation | Heliostat conc. Light | US 2008/0293132 |
| Airlift - flat plate | 65 | Bubbling | | 2011/0159581 |
| Tilted flat plate LED lit + solar | 19 | Spraying algal suspension | Use channels | US 2011/0312062 |
| Tilting flat plate manifold | >100 | Sparging and wave mixing | Creates travelling wave through channels | PCT/US2011/036527 US 2011/0281339 |
| Tilting and ribbed | Variable diaphragm | Fan with bubbling holes | | US 2009/0203067 |

Horizontal Troughs/Ponds

| Raceway | 500 | No mention | Mixing by von Karman vortices | US 2008/086939 |
|---|---|---|---|---|
| Algae inoculated open lagoon | Deep | By bacteria and sparging | Lagoon has co-cultured algae and bacteria | |
| Open V-trough | 600 at bottom | Sparger | Uncovered | US 2009/0215155 |
| Open & covered V-trough | 50-250 | Bubbling lines | | US 2012/0064508 |
| Sequential open troughs | Not stated | Not stated | A propagation concept | PCT/NL01/00273 |
| Solar film covered raceway | Deep | Sparged | Film adsorbs IR | DE 102009015925 |
| Domed pond | Deep | Sparged separately | dimensionless | US2010/255569 |

Tubular

| External-loop tubular | 53 riser 30-160 horizontal | Sparging in attached airlift | Horizontal submerged/ Airlift riser | Acien Fernandez et al. (2001) |
|---|---|---|---|---|
| Double jacketed tubular | Not given | Sparged + Mixing vanes | Use light concentrating parabolic mirror | U.S. Pat. No. 5,958,761 |
| Floating tubular or sleeves | 20-200 | Sparging and mixing | | US2009/0130706 |
| Immersed tubes | 300-1200 | pumped | Inflated side chambers for | PCT/NL/2008/050650 |
| Flexible tubes or sleeves | 150 | Sparging | Circulating algae | US 2008/0311649 |
| Rigid tubes | 10-60 | Not considered | PVC | US 2010/0144023 |
| Rigid tubes | 50-300 | Sparge in separate structure | PVC | US 2011/0104796 |

Sheets/sleeves

| Flexible sleeves on ground | 300 | Flexible diffusers | Paddle wheel mixing | WO 2010/012028 |
|---|---|---|---|---|
| Floating flexible sleeves | Not stated, but not thin layer | "Introduced" | Buoyancy from airspace | WO 2009/087567 |
| Manifolded wide sleeves | 26-150 | "In degas vessel" | Slightly tilted | US 2010/0248333 |
| Flat sheet | 5-30 | Diffusion | | US 2011/0217692 |
| Flat plate/rigid cover/closed | 100-1300 | Sparging | Mixing by flow barriers | US 2009/0068727 |
| Flat sheet | 130-350 | Sparging | In viscous liquid Sonic waves to obtain ripples for better light absorption | US 2011/0092726 |
| Flat sleeve | 25-250 | "Fed" | Water cooled | US 2011/0065157 |
| Flat sleeve | Not stated | Sparge and membrane | Sunlight flickered by lenses and flow | WO 2011086358 |
| Floating sleeves | 20-200 | Pressurized $CO_2$ | Semipermeable under lower sheet | US 2010/0216203 WO 2010/065862 |
| Underwater | Not stated | Bubbling | Pseudo airlift beneath growth chamber | US 2012/0107452 |
| Sleeves on soil | 200-300 | sparger | Roller mixing from top | US 2007/0048848 |

TABLE 1-continued

Designs of sun-lit photobioreactors with insufficient light penetration
to most cells in dense culture and inefficient carbon-dioxide mixing

| Photobioreactor configuration | Optical path thickness (mm) | Carbon dioxide supply | Comments | Reference[c] |
|---|---|---|---|---|
| Covered raceway floating or on ground | 200 | Spraying algae to headspace &sparging | rigid cover/ | U.S. Pat. No. 8,110,395 |
| Circular floating covered ponds | >>20 mm rod diameter (ns) | Sparger in rods | Mixing by rotating rods | US 2012/0115210 |
| Floating tubes in mat | Not stated | Sparger in recycle reservoir | Fish eat biofilm | Appl GB 2473865 |
| Floating sleeves | 200 | Sparger or fountain | Many possible mixers cited | US 2008/0009055 |
| Submersible floating sleeves | 50 | Sparger or diffusion | Multi-compartmented | US 2011/0124087 |

[a]Bioreactors predominantly illuminated internally or externally by fluorescent, LED, fiber-optics etc. artificial light are excluded from this table.
[b]Only representative examples of super-structure requiring vertical and incline photobioreactors are given, because they are not the subject of this application
[c]Non-patent citations are listed at the end of the application in the general references Bioreactors predominantly illuminated internally or externally by fluorescent, LED, fiber-optics etc. artificial light are excluded from this table.

b Only representative examples of super-structure requiring vertical and incline photobioreactors are given, because they are not the subject of this application c Non-patent citations are listed at the end of the application in the general references Water adsorbs infrared radiation from the sun. At a depth of 5 cm ca. 90% of the near-infra-red (most of the infrared from the sun, and the part with the greatest energy) is adsorbed, resulting in heating the algae above their optimum growth temperature in many environments, and at 50 cm 99% would be adsorbed resulting in considerable heating. At 5 mm only 9% would be adsorbed in a floating bioreactor, and the rest would penetrate to the water below, easing the cooling and heat exchange.

The bubbling in many photobioreactor (PBR) designs is for two reasons—to mix algae and keep them suspended, and to introduce $CO_2$. The $CO_2$ in previous systems must often be diluted with air because at higher concentrations $CO_2$, the bubbling rate required for mixing would overly acidify the medium. This is especially a problem with larger celled algae, as they settle more quickly than small-celled algae, and more mixing energy is required. Large volumes of $CO_2$-enriched air are thus pumped at high energy costs, losing much of the $CO_2$. The present invention precludes the need for using bubbles for mixing and reduces the cost of $CO_2$, sterile medium, harvesting, and produces less effluent if medium after harvest is not recycled. Methods other than sparge bubbling have also been proposed; e.g. mixing the carbon dioxide with the medium being introduced by co-flowing over a solid substrate, and (un-economically) adding NaOH to the medium to capture atmospheric $CO_2$ and thereby generate bicarbonate (EP 2 371 940).

Many closed vertical systems constructed above ground are made of rigid or flexible sheets, tubes, plastic bags/sleeves, or glass walls are described in Table 1. Such structures allow more concentrated growth, and use efficient (but high compression cost) bubbling of carbon dioxide mixed air. The capital costs of the rigid materials are high, as are superstructure costs to assure that they will not be destroyed in high winds. Evaporative cooling from the culture media is impossible in closed systems, and as the water in the structures absorbs infrared light, and cooling can be expensive. Short optical paths can be designed in such systems, allowing increased density of algae (Table 1).

Horizontal or near horizontal systems (Table 1) allow for less superstructure. One system (US2007/0048848) uses recumbent flexible plastic sleeves with mixing affected by a track support of peristaltic rollers, with no explanation of how temperature is to be controlled. In another (dimensionless) system, a gas plug is moved through channels by somehow tilting the system to move a gas plug along through the system as a standing wave (US2011/0281339). The density of algal cells and method of cooling is not disclosed therein, and there are superstructures required to perform the tilting.

Totally horizontal systems (Table 1) using plastic film are far less expensive, and are used floating on the sea, where wave motion provides some mixing and the seawater provides the cooling. Both are appropriate only for fresh water algae as they achieve their buoyancy by floating the bioreactors on seawater, using the specific gravity differences to keep them afloat. Carbon dioxide mixed with air is pressure bubbled through the system using spargers, and significant amounts are wasted, as in the other systems. An optical path of 10-15 cm is needed to optimally use the carbon dioxide. There is no horizontal system reported where the depth of algae is less than 5 cm or where carbon dioxide is provided other than by sparging, and where excess oxygen is removed by any process other than venting (Table 1).

SUMMARY OF THE INVENTION

A thin layer horizontal system is disclosed herein where cooling is provided by floatation on water, where part of the solar infrared irradiation passes through the bioreactor into the water, and the rest is dissipated through the bottom thin layer of floating plastic sheeting acting as a heat exchanger (FIGS. 1 and 2A, B and C). Buoyancy is achieved by having a gas space above the algae, and thus marine algae in seawater can be cultivated above any type of water. Optimal light utilization is achieved by situating the algae in a thin, highly concentrated layer. Carbon dioxide is transferred from the gas space by wave motion eliminating the need for compressed carbon dioxide bubbles. Rapid diffusion of the carbon dioxide into the thin layer of algae (less than 1 cm in depth) is effected by various types of wave motion, including wave machine imposed waves, which can be augmented by fins attached to the bottom of the bioreactor, or mini-waves generated by vibrators or piezo-electric devices attached to the bottom sheet (FIGS. 3-9), or by using a bottom sheet that is rocked by low amplitude vibrations (FIG. 10). The types of waves that the agitation/excitation devices produce are crucial to the gas-algae mixing process. The frequency component of these waves must not inhibit algal growth processes; thus such ultrasonic frequencies within the mechanical excitation pulses produced by the piezoelectric or magneto-strictive devices must be avoided. Inducing shear waves forms larger inner layer gas algae interface areas and thus accelerate the mixing and micro organic processes. The device activation must be timed to produce the near shear waves and turbulent vortices that promote gas-algae mixing.

The thin-layer photobioreactor (TLPBR) is constructed from inexpensive plastic sheeting fabricated into wide sleeves, flexibly held flat floating over the cooling water. The excess oxygen emitted by photosynthesis can either purified and used in industrial processes or released to the atmosphere by through plastic sheeting that has an extensive permeability to oxygen but is less or impermeable to carbon dioxide (low beta value). The high density of algae requires less sterilized culture medium and facilitates the use of highly inexpensive flocculation technologies for harvesting the algae. No above ground superstructure or high pressure pumping are required.

One embodiment of the present invention provides a photobioreactor for cultivating and growing microalgae comprising flexible plastic sheeting having a first and second face wherein said first (lower) face is coated with a layer of microalgae less than 1 cm in thickness and floats on the surface of a heat dissipating body of water with inlet and outlet opening for inserting algal inoculum and medium, and for harvesting excess algae (FIGS. 1 and 2A, B and C). The said second (upper) face of flexible sheeting contains a gas space. The gas space above contains a predetermined span of ratios of carbon dioxide to oxygen and a means for increasing the pressure of the gas space with inlet and outlet openings. A source of light is above the second (upper face), which may preferably be sunlight, or sunlight augmented with artificial illumination or artificial illumination alone. Below or attached to the lower face is a means for agitating the body of water and the algae in the bioreactor, facilitating gas exchange with the airspace, and heat exchange between the algal layer and the subtending water. Preferably the thickness of the microalgae coating is in the range of 2.5 to 5.0 mm.

Another embodiment of the present invention provides a process for cultivating and growing microalgae comprising the steps of:
(a) providing a photobioreactor comprising flexible plastic sheeting sealed as a container or tubular flat sleeve having a first and second face as described above said flexible sheeting comprising a predetermined amount of carbon dioxide and a body of heat exchanging water beneath and in contact with the sheeting;
(b) coating the sheeting on said first face with a layer of microalgae less than 1 cm in thickness;
(c) floating the first face of the sheeting on the surface of a body of heat dissipating water by virtue of having a gas space between the two faces providing buoyancy;
(d) mechanically agitating the body of water causing vibrations and a wave-like motion using low amplitude wave generators (FIG. 3) where the spacing and timing of the transducers that generate the wave pulses can be set such that they generate near shear waves that facilitate mixing and gas exchange in the algae layer.
(e) these waves allow the carbon dioxide in the air space to dissolve in the aqueous mineral medium containing the algae and release the oxygen formed during photosynthesis to the airspace above;
(f) exposing the microalgae to light; and
(g) harvesting microalgae by exerting pressure between the sheeting and forcing the microalgae out of the photobioreactor through a suitable opening. In another embodiment the photobioreactor is comprised of algae and/or cyanobacteria selected from *Phaeodactylum tricornutum, Amphiprora hyaline, Amphora* spp., *Chaetoceros muelleri, Navicula saprophila, Nitzschia* sp., *Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleo abundans, Synechococcus elongatus* PCC 6301, *Botryococcus braunii, Gloeobacter violaceus* PCC CC742, *Synechococcus* PCC 7002, *Synechococcus* PCC 7942, *Synechocystis* PCC 6803, *Thermosynechococcus elongatus* BP-1, *Nannochloropsis oculata, Nannochloropsis salina, Nannochloropsis* spp., *Nannochloropsis gaditana, Isochrysis* aff. *galbana, Aphanocapsa* sp., *Botryococcus sudeticus, Euglena gracilis, Nitzschia palea, Pleurochrysis carterae, Tetraselmis chui, Pavlova* spp., and *Nannochloris* spp., as representatives of all algae and cyanobacteria species; preferably, the algae is freshwater *Chlorella* sp. or *Chlamydomonas reinhardtii* or *Synechococcus* sp. PCC 7002 (marine) or *Synechococcus* 7942 (freshwater) or *Nannochloris* sp., or *Nannochloropsis* spp., *orlsochrysis* sp. CS-177, or *Pavlovalutheri*, or *Phaeodactylum tricornutum*, or *Tetraselmis chui*, or any combination thereof.

In another embodiment the photobioreactor is comprised of fins attached beneath the lower plastic sheeting amplifying the movements caused by the mechanical wave generator or natural waves when floating on open water (FIG. 4), or causing reciprocal movement due to continuous or pulsed unidirectional water flow when tethered or rivers of artificial channels (FIG. 5). The fins can be set at specified distances such that they generate near shear waves that intensify and mix the algae layer. These near shear waves that form increase the gas-algae interface, facilitating efficient gas exchange between the air space and the algae growth medium. In all embodiments of the present invention provides a photobioreactor as described hereinabove wherein the pH of the water is maintained at the daytime optimum for photosynthesis for the particular algal species being cultivated (typically pH 6.5) through control of the amount of dissolved carbon dioxide, by controlling the production of waves through a feedback, where are artificially generated, and controlling the tautness of the tethers to limit or increase flexibility and mixing in bioreactors floating on natural wave generating bodies of water.

In another embodiment the present invention provides a photobioreactor as described hereinabove wherein the temperature of the body of water is maintained at the optimum temperature for each species of algae through the use of heat exchange through the lower layer, through the use of river, sea or artificially cooled water in warm climates, or warm water from industrial effluent cooling water or other sources in winter in temperate climates.

In another embodiment the present invention provides a photobioreactor as described hereinabove wherein the water agitation is generated by piezoelectric wires in a mesh formation (FIG. 6A) or as spread out single transducers inside the algal suspension (FIG. 6B).

In another embodiment the present invention provides a photobioreactor as described hereinabove wherein the exposure to light is comprised of a light intensity from about 200

μEin/m²/s to full sunlight and a light to dark ratio of about 16 to 8 hr, or ambient natural light dark ratios.

In another embodiment the present invention provides a photobioreactor as described hereinabove wherein the water agitation is generated by a series of mini-vibrators (FIGS. 7 and 8A, B, C and D).

In the basic configuration put forth and detailed in FIGS. 8A and 8B the control of timing of excitation of individual mini-vibrators is pre-programmed to generate near shear waves. The mini-vibrators can be mounted glued to the underside of the photobioreactor (FIG. 8A) or mounted inside rigid profiles that contribute to a near sag-free surface inside the photobioreactor (FIG. 8B). A localized control method of controlling the creation of near shear waves is described in FIGS. 8C and 8D. A hydrophone senses the arrival of a wave from an adjacent mini-vibrator or transducer (piezoelectric or magnetostrictive) and activates the mini-vibrator and enhances the amplitude of the traversing near shear wave.

In another embodiment strips of plastic bubble material are affixed to the bottom of the bioreactor to prevent sag caused by the positive pressure in the airspace, and the weight of the mixing devices (FIG. 9).

In another embodiment the bottom of the photobioreactor is reinforced with rigid plastic and trussed beams, and the waves are generated by vibrational rocking of the structure (FIG. 10).

In the preferred embodiments where waves are artificially generated, the timing of the wave pulses can be set such that they generate near shear waves that mix the algae layer. The near shear waves that are so formed increase the gas-algae interface area, thus facilitating efficient gas exchange between the air space and the algae growth medium.

In preferred embodiments the preferred plastics will have a low beta value, i.e. will pass oxygen and retain carbon dioxide, thus venting excess oxygen when the airspace exceeds the 20% oxygen in the outside atmosphere; preferred plastics are based upon one or more of the following polymers and copolymers and/or laminates thereof optionally blended with plasticizers and anti oxidants: polyethylene, polypropylene, polybutylene, polycarbonate, polyester, polyamide, polyvinyl chloride, polyvinylidene chloride, polystyrene copolymers of butadiene and styrene, polyurethane, polyacrylonitrile and polyacrylate in single or mixed multilayer sheets.

In a preferred embodiment the top plastic is suitably treated to prevent degradation by ultraviolet light, reflects the maximum amount of infrared light possible (to reduce cooling cost) without overly reducing transmission of photosynthetically active irradiation, and does not support having light-reflecting condensate on the inner side. The top plastic in a preferred embodiment is specially treated to transmit (and not reflect) low angle light in early morning and late afternoon.

In the embodiments where 100% carbon dioxide is the starting gas, molecular sieve filtration system may be used to remove the oxygen emitted during photosynthesis (as a valuable co-product) and then the plastic used will be chosen to have the least possible permeability to all gases.

In other embodiments the upper plastic layer will be a low beta value plastic that transmits oxygen and retains carbon dioxide, preventing inhibition of photosynthesis by excess oxygen and precluding the need to periodically vent the bioreactors to remove excess oxygen (and lose some carbon dioxide) or necessitate the more expensive molecular sieve filtration.

In preferred embodiments, harvesting will be performed at intervals based on photometric density determination of the algae removing 25-50% of the algae containing fluid, and immediately replacing the fluid with essential mineral (fertilizer) augmented sea or fresh water based medium (depending on the algal species used). The essential mineral (fertilizer) augmented sea or fresh water based medium is commonly referred to as an aqueous medium. When microalgae are introduced into the aqueous medium, the combination can be referred to as a thin aqueous microalgae layer. The preferred algal species used are those that rapidly remove and internally store essential elements from the medium for future use, as they compete best with unwanted species. The amount of fertilizer added is just enough not to limit growth, and have all essential elements removed and utilized by the algae prior to the next harvesting cycle, such that there is minuscule fertilizer wastage, and less problem of fertilizer in effluents.

The bottom plastic in preferred embodiments will be of a plastic having the maximum cost-effective rate of heat exchange. When transgenic herbicide resistant algae are used, the inner surface layer of the bottom plastic may be impregnated with the appropriate herbicide to facilitate slow release to control alien species. The inner layers of the top and bottom plastic sheets may be impregnated with non-phytotoxic fungicides and anti-microbials to allow slow release and prevention of contamination and biofilm formation. In one embodiment semi-rigid flexible fins are attached to the bottom plastic perpendicular to the direction of water flow. By having the water flow in waves or controlled surges, the fins will wiggle the bottom plastic facilitating the continuous suspension of the algae and the introduction and dissolution of the carbon dioxide into the media (FIGS. 4, 5). The intensity and the frequencies of the pulsed surges are feedback controlled by the pH and temperature sensors to control $CO_2$ and temperature in the photobioreactor. The intensity of mixing can be further dampened or increased by servo-mechanically adjusting the tension on the tethering ropes. In a sea situation, the tidal movement can be used to flutter the fins as the tide comes in/goes out. In unidirectional flow systems (floating on rivers, on land, on flood plains) the water movement can be used to flutter the system.

In all the embodiments harvesting is accelerated by the positive pressure of the gas space above the algae in the photobioreactor, that expels the algae into the opened harvest outlet.

The fresh, brackish, or marine algae and cyanobacteria can be (non-exclusively) selected from the following list:

In the various embodiments, algae and cyanobacteria were chosen from the following organisms: *Phaeodactylum tricornutum, Amphiprora hyaline, Amphora* spp., *Chaetoceros muelleri, Naviculasaprophila, Nitzschia* sp., *Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleo abundans, Synechococcus elongatus* PCC 6301, *Botryococcus braunii,*

*Gloeobacterviolaceus* PCC 742, *Synechococcus* PCC 7002, *Synechococcus* PCC 7942, *Synechocystis* PCC 6803, *Thermosynechococcus elongatus* BP-1, *Nannochloropsis oculata, Nannochloropsis salina, Nannochloropsis* spp., *Nannochloropsis gaditana, Isochrysis* aff. *galbana, Aphanocapsa* sp., *Botryococcus sudeticus, Euglena gracilis, Nitzschiapalea, Pleurochrysis* carterae, *Tetraselmis chuii, Pavlova* spp. and *Nannochloris* spp. as representatives of all algae and cyanobacteria species. The algae come from a large taxonomical cross section of species (see Table 2 below).

TABLE 2

Phylogeny of some of the eukaryotic algae used

| Genus | Family | Order | Phylum | Sub-Kingdom |
|---|---|---|---|---|
| *Chlamydomonas* | Chlamydomonadaceae | Volvocales | Chlorophyta | Viridaeplantae |
| *Nannochloris* | Coccomyxaceae | Chlorococcales | Chlorophyta | Viridaeplantae |
| *Tetraselmis* | Chlorodendraceae | Chlorodendrales | Chlorophyta | Viridaeplantae |
| *Phaeodactylum* | Phaeodactylaceae | Naviculales | Bacillariophyta | Chromobiota |
| *Nannochloropsis* | Monodopsidaceae | Eustigmatales | Heterokontophyta | Chromobiota |
| *Pavlova* | Pavlovaceae | Pavlovales | Haptophyta | Chromobiota |
| *Isochrysis* | Isochrysidaceae | Isochrysidales | Haptophyta | Chromobiota |

Phylogeny according to: http://www.alqaebase.org/browse/taxonomv/

It is however, clear for one skilled in the art that this list is not exclusive, but that various other genera and species can be used as well.

The smaller unicellular species are typically/usually preferred, as they can be kept suspended in solution with the minimum amount of energy. With minor modification in the harvesting system, the growth structures can be used for cultivation of small water plants such as duckweeds (Lemnaceae). Instead of pressuring material to be harvested through a port in the bottom sheet, a skimming device is used to harvest the duckweeds.

In all embodiments the algae used can be wild type isolates or mixed species, or they can be genetically engineered to have traits that increase reliability in culture (see Table 3 below), or that provide value added to the algae (see Table 4 below).

TABLE 3

Examples of transgenes that increase reliability in culture

| Trait | Gene or Gene Product |
|---|---|
| Herbicide resistance for resistance to algal contamination | |
| glyphosate | Modified epsp synthase |
| glufosinate | Bar or Pat |
| fluorochloridone | Mutant phytoenedesaturase |
| butafenacil | Mutant protoporphyrinogen oxidase |
| Resistance to microorganisms | |
| Bacteria/fungi | |
| antimicrobial proteins | e.g. lactoferricin |
| Viruses | |
| RNAi or overexpression | Specific pieces of viral DNA or cDNA |
| Resistance to *zooplankton* | |
| protozoans | antimicrobial peptides |
| sea lice | avermectins |
| No quorum sensing | anti apoptosis genes |
| Maximum growth | |
| smallerPSII antennae | tla 1gene |
| systems/synthetic biology | New light reactions |
| | New dark reactions |
| Heat tolerance | psbAdouble mutant and/or polygenes |
| Inability to grow in nature | |
| | Δ carbonic anhydrase |
| | Δ nitrate/nitrate reductase |
| | Partially suppressed Rubisco |

Δ = deleted section of gene resulting in inactivity.
Source: Gressel (2013)

TABLE 4

Examples of transgenes conferring added economic value to algae

| Trait | Gene or gene product |
|---|---|
| Modify lipids for biofuels | various |
| Hydrogen production | various |
| Enhancing digestibility | antisense or RNAi of cell wall glycosyltransferases |
| Enhancing digestibility | introduce vacuolar or periplasmic sequestered carbohydrases |
| Increasing methionine content | modifiedcystathionine synthase + zein peptide |
| Increasing lysine content | feedback insensitive dihydrodipicolinate synthase |
| Enriching/modifying omega 3 and omega 6 fatty acids | ALA, EPAelongases and desaturases |
| Release bound phosphate, Fe, Zn in feeds or digestive track | phytase |
| Increase iron content | inactive or active ferritin |
| Increase Cu and Zn | inactiveCuZn superoxide dismutase |
| Bioplastics | phbB and phbC encoding poly-3-hydroxybutyrate |
| Other industrial feedstocks | various |
| Replace feed efficiency enhancing antibiotics | antimicrobial peptides |
| Controlling sea lice | avermectins |
| Vaccines and therapeutic proteins | various genes |
| Increased growth rate of fish | fish growth hormone |

Source: Gressel et al. (2013)

It is however, clear for one skilled in the art that the examples of possible transgenes listed in Tables 3 and 4 are not exclusive, and various other genera, species of algae, and small aquatic plants can be cultivated as well.

In all embodiments, the density of the algae should be sufficient that the inexpensive flocculation system described by Schlesinger et al. (2012) can be used, and the effluent water recycled back into the culture system after adding concentrated fertilizer.

The ideal places for the cultivation of algae in the photobioreactors are:

(1) On river flood plains where crops cannot be reliably cultivated. Cooling water can be supplied by gravity from weirs begun upstream;
(2) Structures akin to rice paddies or such as abandoned shrimp farms near the sea with added pumping systems;
(3) Floating in rivers;
(4) In protected bays or estuaries;
(5) In temperate climates: near power plants, near hot springs or other sources of hot water that can be a source of warm water in winter, as well as provide carbon dioxide
(6) In open seas with system to lower bioreactors deep into the sea in stormy weather (U.S. 2011/0124087). In this case the airspace will have to mostly emptied prior to sinking, and re-floating can be facilitated by pumping in gas. Since the algae in the photobioreactors adsorb virtually all photons, the best locations are where there is maximal irradiation, deserts (preferably near the sea)+30° N/S from the equator.

(7) These photobioreactors allow covering of water reservoirs, whether for drinking or for irrigation or industrial use, where they have certain advantages:
1. By covering the surface they prevent evaporative water loss, and do so without cost to the reservoir owner, as the algae are being commercially cultivated, and;
2. By having the algae form a layer that is not penetrated by light, photosynthetic algae and cyanobacteria cannot grow in the reservoir water, precluding the production of toxins and other undesirable compounds by algae and cyanobacteria.

BRIEF DESCRIPTION OF THE DRAWINGS

The figures are not-to-scale illustrations of the thin-layer photobioreactors that are the subject of this patent.

FIG. 4 is a modified version of the photobioreactor shown in FIG. 3 whereby flexible fins are attached to the bottom of the bioreactor to augment and optimize the wave action of waves generated by the wave machine, to amplify the vibration of the bioreactor and thus cause greater wave motion. It consists of: 2-3 mm thick, 2-4 cm wide plastic strips pre-embedded by folding and welding or adhesive sealing to the lower plastic sheets across the width of the sleeve when waves are to be generated over the length of the bioreactor (and then will also prevent sagging in the middle of the bio-reactor), or across the length of the bioreactor if the waves are generated from the sides. The fins are spaced in parallel 20-90 cm apart, preferably 25-50 cm apart;

FIG. 5 is a modified version of the photobioreactor shown in FIG. 3 whereby flexible fins are attached to the bottom of the bioreactor to augment and optimize the wave action of waves generated by unidirectional flowing water to amplify the vibration of the bioreactor and thus cause greater wave motion. It consists of: 2-3 mm thick, 2-4 cm wide plastic strips pre-embedded by folding and welding or adhesive sealing to the lower plastic sheets across the width of the sleeve when waves are to be generated over the length of the bioreactor (and then will also prevent sagging in the middle of the bio-reactor), or across the length of the bioreactor if the waves are generated from the sides. The fins are spaced in parallel 20-90 cm apart, preferably 25-50 cm apart, with unequal spacing calculated to form near shear waves;

FIG. 9 is a modified version of the photobioreactor shown in FIGS. 3-5 whereby rows of plastic bubbles (similar to bubble wrap used in packing) are attached by adhesive or are welded to the bottom facing the cooling water) to further prevent sag in the middle of the bioreactors;

DETAILS OF THE INVENTION

The present subject matter may be understood more readily by reference to the following detailed description taken in connection with the accompanying figures and examples, which form a part of this disclosure. It is to be understood that this subject matter is not limited to the specific devices, methods, applications, conditions or parameters described and/or shown herein, and that the terminology used herein is for the purpose of describing particular embodiments by way of example only, and is not intended to be limiting of the claimed subject matter.

As used in the specification including the appended claims, the singular forms "a", "an", and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about", it will be understood that the particular value forms another embodiment. All ranges are inclusive and combinable.

EXAMPLES

The algae used in the following examples, their growth media, and the mode of culture before seeding in the photobioreactors are described below:

Algal species used in the following examples Freshwater *Chlorella* sp. and *Chlamydomonas reinhardtii*, and *Synechococcus* PCC 7002 (marine), *Synechococcus* 7942 (freshwater), *Nannochloris* sp., *Nannochloropsis* spp. *sochrysis* sp. CS-177, *Pavlova lutheri*, *Phaeodactylum tricornutum* and *Tetraselmis chui* are used in the examples below.

Algal Cultivation for Seeding

Algae were cultured indoors in 2 L polyethylene sleeves. A constant temperature regime was maintained at 23° C., light:dark was set at 16:8 h, light intensity of 200 µEin/m²/s. Cultures were mixed by aeration using 4% $CO_2$ mixed into air during the day and delivered to the cultures at a controlled rate via the aeration system to maintain pH7. During the dark period air alone was bubbled.

Culture Media

Marine algal species and *Synechococcus* PCC 7002 were cultured in the laboratory in 0.45 µm ultra-filtered seawater enriched with F/2 nutrient enrichment (Guillard and Rhyther, 1962), and out of doors a commercial fertilizer mix diluted 1000 fold with UV-sterilized seawater. The concentrated commercial fertilizer contained (in meq.) 703 $N03^{-1}$, 268 $NH4^{-1}$, 213 P205, 771 K20, 604 $Ca^{+2}$, 229 $Mg^{+2}$, 13 $Fe^{+2}$, 6.6 $Mn^{+2}$, 2.8 $Zn^{+2}$, 0.4 $Cu^{+2}$, 0.2 Mo (calculated from brochure of supplier). *Chlamydomonas reinhardtii* was cultured in 0.45 µm ultra-filtered TAP culture medium (Gorman and Levine, 1965). *Synechococcus* 7942 was cultured in 0.45 µm ultra-filtered BG11 culture medium (http://www-.crbip.pasteur.fr/fiches/fichemedium.jsp?id=539, accessed 1 Jun. 2012).

Example 1 Laboratory Proof of Concept

Figure 11:
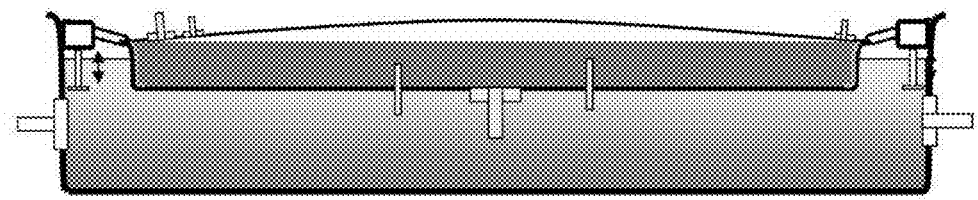
FIG. 11 is an illustration of a laboratory scale exemplary and non-limiting thin layer floating on water photobioreactor.
Figure 12:
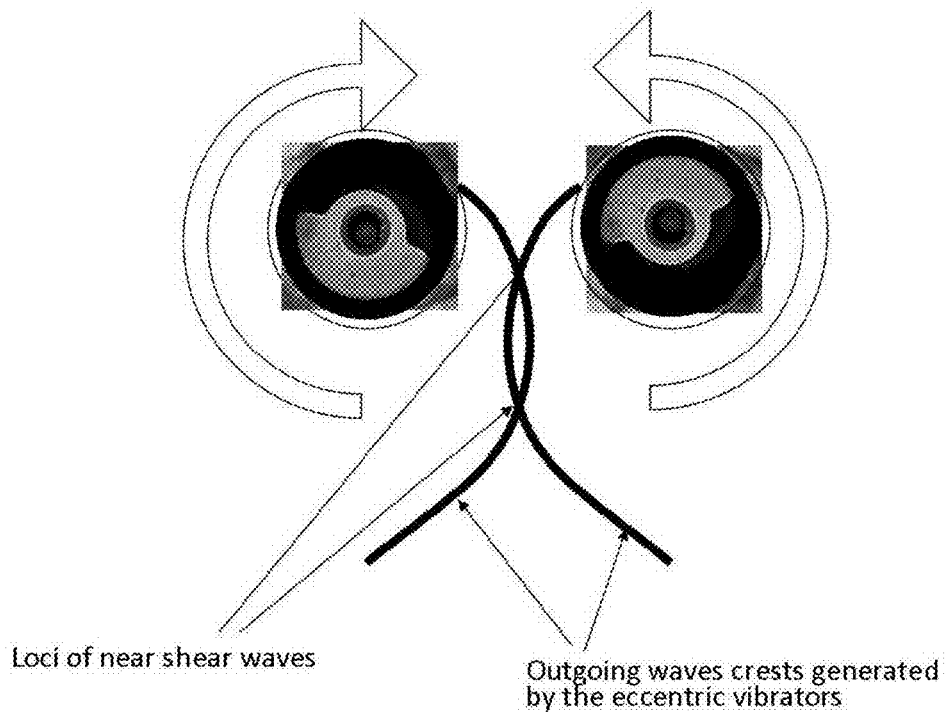
FIG. 12. Diagram demonstrating how vibrating pulses on the plastic sheet generate near shear waves at the point where waves from each pulse meet.
Figure 13:
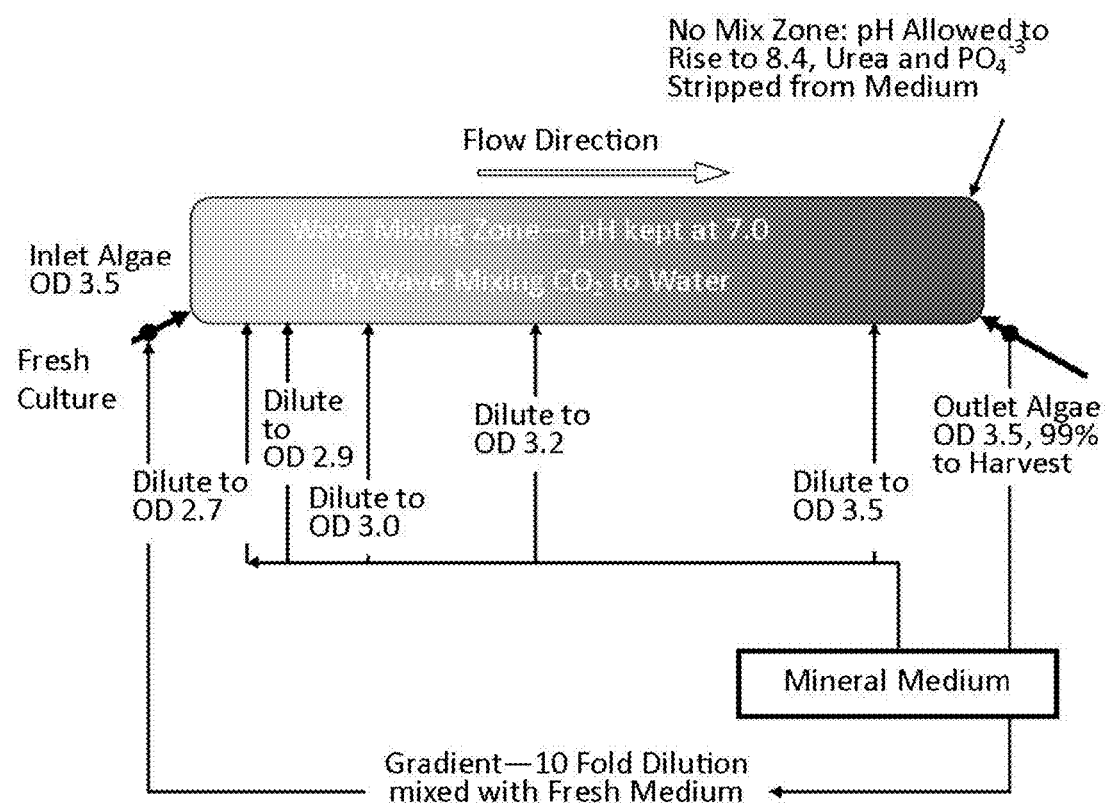
FIG. 13. Configuration of medium introduction into a photobioreactor. Medium is introduced at places where a doubled concentration of algae is reached by controlling flow rate of introduced algae and medium. The medium minerals are introduced at a rate where they are depleted by the time of algae doubling. This generates a slowly moving plug of algae towards the harvesting aperture. The length of the last phase before algae are forced out of the harvesting aperture can be varied based on whether a phase of stationary growth is desired to force metabolism of specialty products, e.g. increased secondary metabolites or neutral lipids.
Figure 14:
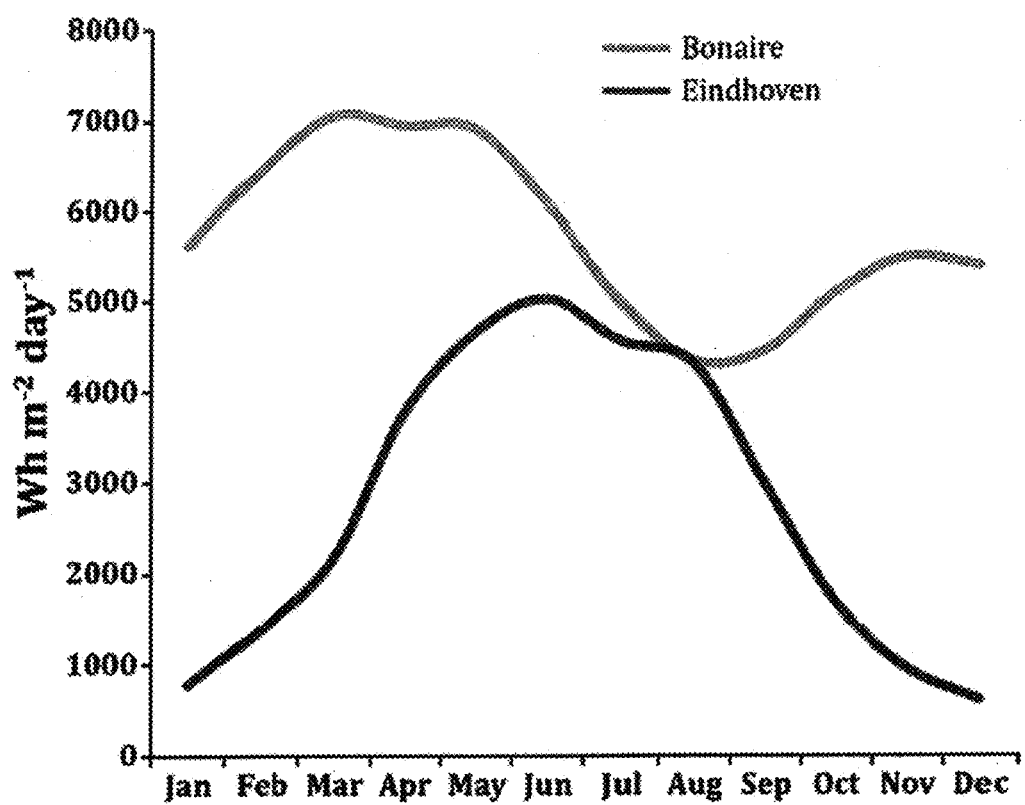
FIG. 14 Sensitivity analysis comparing temperate climate results with a more tropical setting.

As shown in FIG. 11, a large plastic basin filled ⅔ with water was fitted with a 4×4 cm wooden board the width of the basin with a rod mounted perpendicular to the center of a long side of the board. The rod was mounted through a plastic pipe just larger than the rod, acting as a bearing to ensure up and down motion. The rod was attached to eccentric cam via a short rod with bearings at either end, on a slow, adjustable motor, such that when the motor is activated, the up and down movement on the board generated waves.

Grommets are welded ca. 1 cm below the seams on sealed ends food-grade polyethylene sleeve (typically but not exclusively) 0.5 mm thickness) such that it could be loosely or spring-tethered flat on the water with thick rubber bands. Various sealable ports are inserted in the upper sheet of the sleeve: an inlet for medium, an inlet for $CO_2$, an outlet with pressure valve that keeps the airspace inflated and releases excess gas, an inlet through which a mini-pH electrode is inserted with its tip near the bottom of the flat sleeve. In various experiments algae at a density of ca. $10^8$ cells/ml and an absorbancy at 695 nm of ca. 3.0 (based on 1 cm light path) are introduced (the actual values depend on the species used). In various runs fresh water *Chlamydomonas* and *Chlorella*, marine *Nannochloropsis* and *Nannochloris* algae and fresh water *Synechococcus* 7942 (*Cyanobacterium*) are used. In various experiments a 3-7 mm layer of algae were introduced. The sleeve's air space above the algae was flushed with 100% $CO_2$ and then using a flow valve, a slow rate of 10 liters per hour. The pH electrode inserted into the algal suspension was attached to an aquarium pH controller, which is used to actuate the motor creating the waves when photosynthetic use of carbon dioxide rises above pH to 7.5 and the wave generator remains on until the pH is lowered to 6.5.

The container underneath the algae has heat exchanging cooling coils attached to a commercial water cooler and pump, allowing temperature control of the water below the suspended sleeve to culture each species at its optimum temperature.

Experiments are run for four days, with daily removal of samples, and measurements of cell density. The volume of algae to remove with the subsequent addition of an equal volume of fresh medium is calculated to return to the starting cell density. The medium is preferably an essential mineral (fertilizer) augmented sea or fresh water based medium, which is commonly referred to as an aqueous medium. The combination of microalgae and the aqueous medium can be referred to as a thin aqueous microalgae layer. The algae and cyanobacteria that were wave mixed grew at near maximal rate with nearly the best yields achievable with bubbling $CO_2$. Static, control cultivated algae, cultured without wave motion failed to grow. Example 2 Larger scale pilot experimental proof of concept, choice of best plastics.

Figure 1:
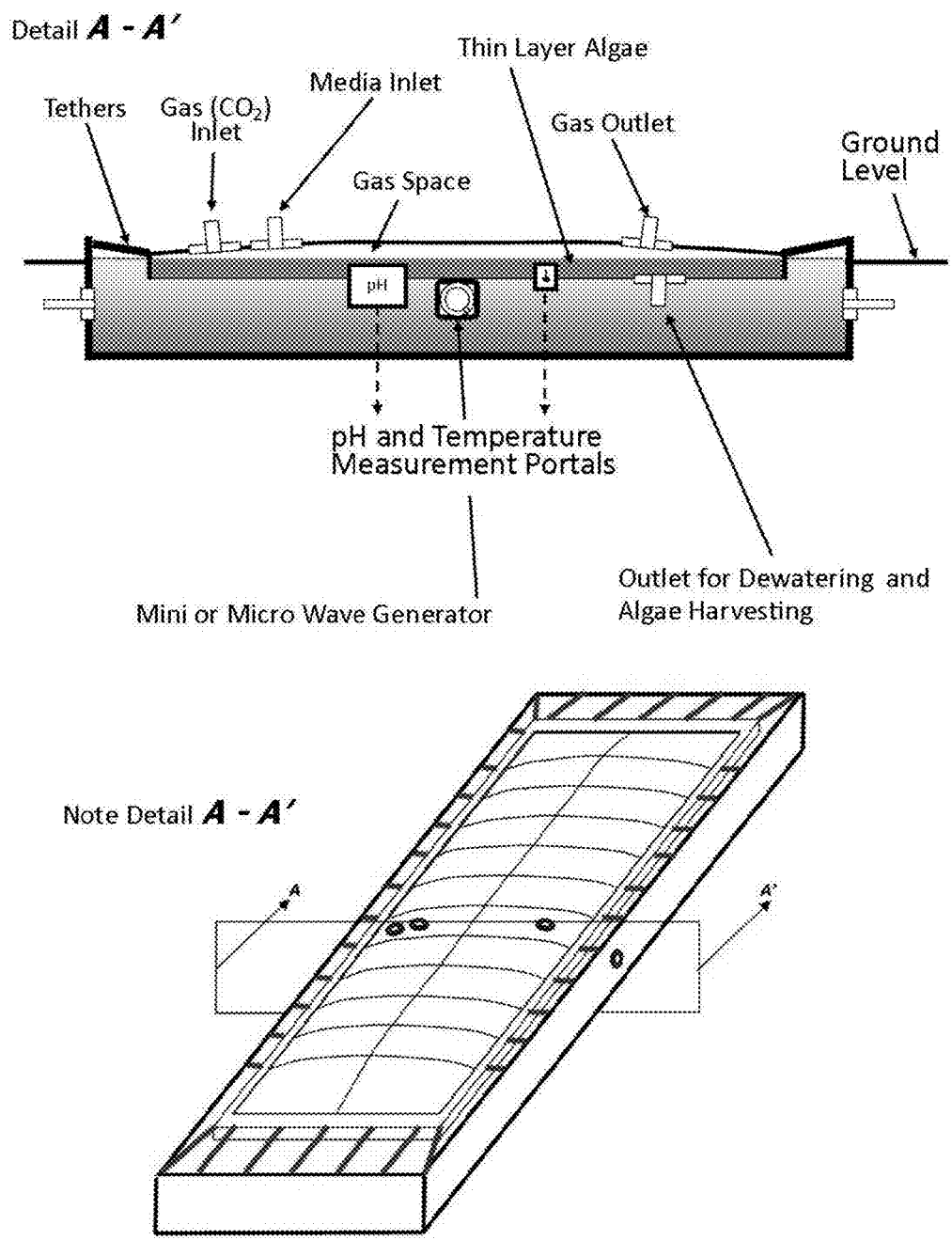
FIG. 1 is a generic view of a thin-layer photobioreactor not showing how wave mixing is achieved. Other figures show various methods of achieving wave motion mixing.
Figure 2A:
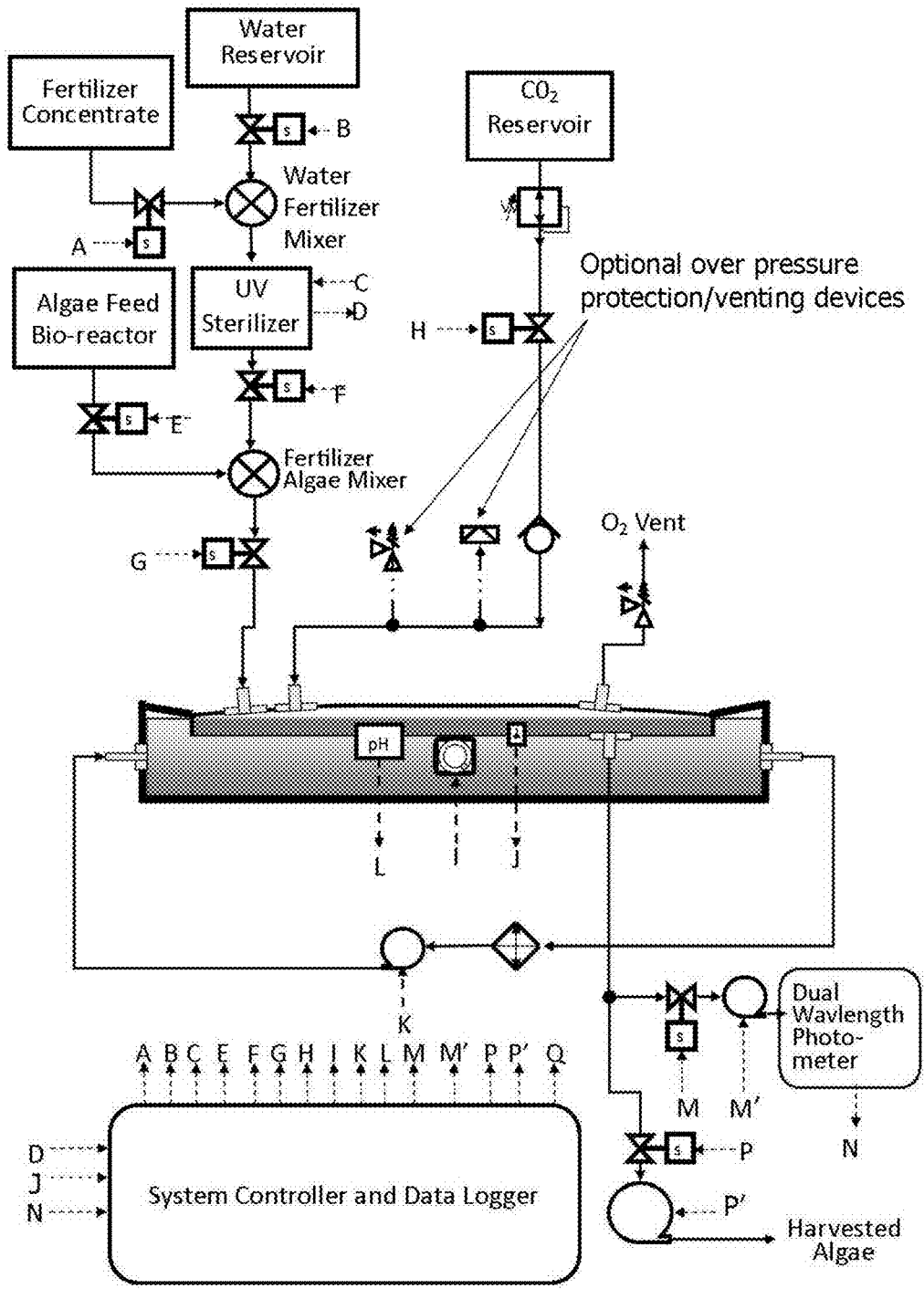
FIGS. 2A, B and C show the peripheral controls and the photobioreactor as part of a system of commercial algal production. A. the systems controls; B. the components of the system; C. the necessary data logging to control the system.
Figure 2C:
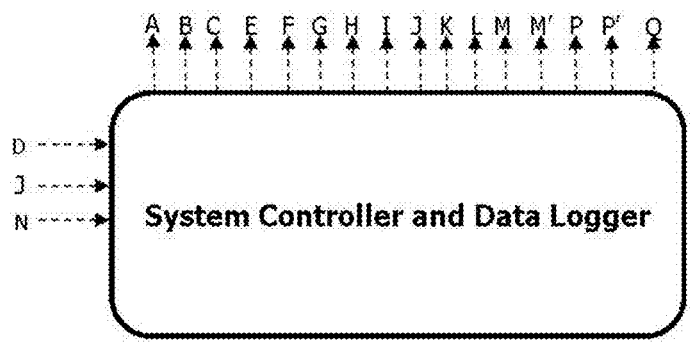
Figure 3:
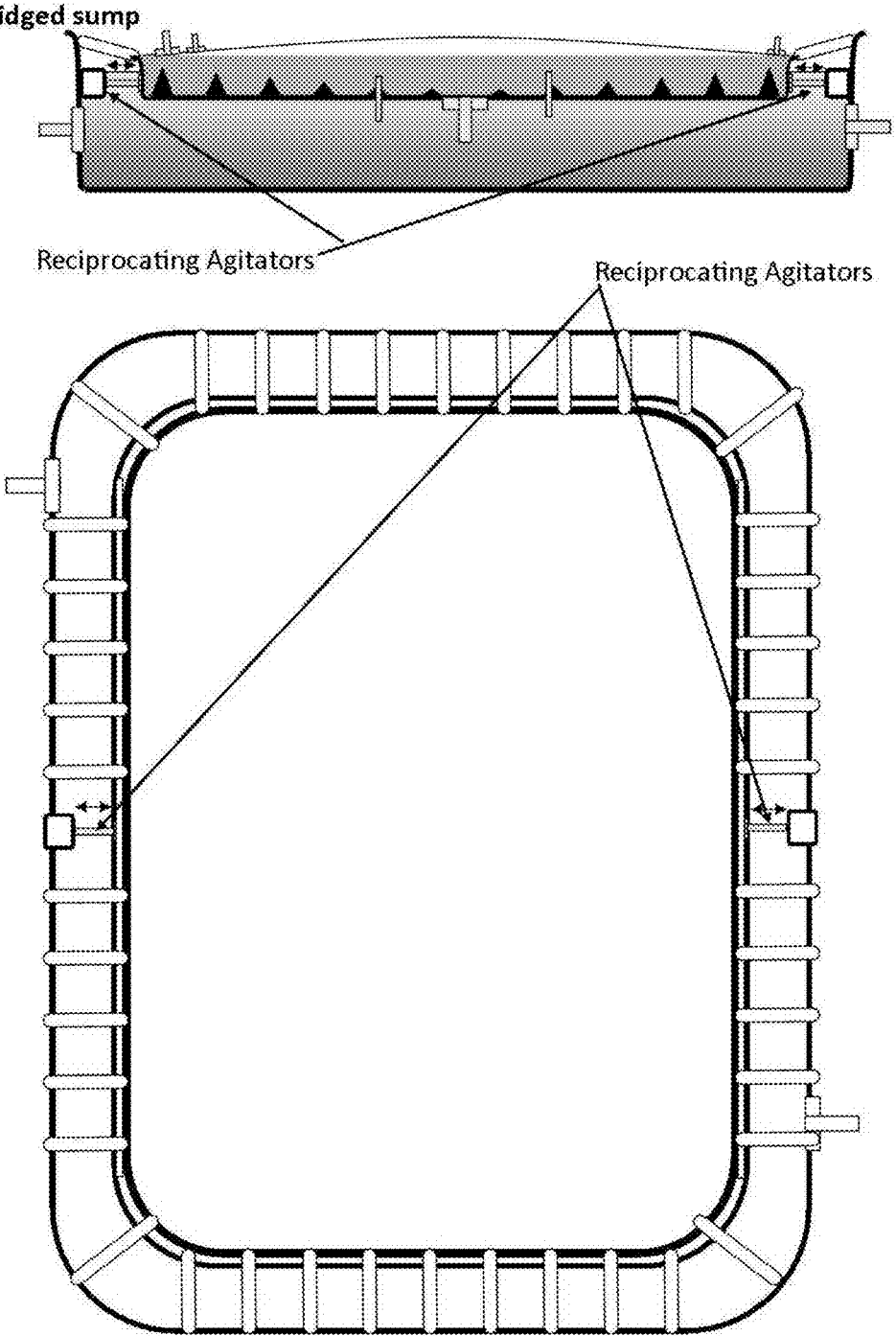
FIG. 3 is a pilot scale photobioreactor that can be expanded in length for larger scale production. It includes the functions shown in FIGS. 1 and 2A, B and C. The low amplitude (mini)waves are formed by mechanical eccentric piston driven wave generators at the side(s) of the bioreactors, actuated electronically when the pH rises above a fixed value for each species to generate shear) waves to optimally dissolve carbon dioxide from the airspace and lower the pH.

The same design with somewhat more sophisticated apparatus is tested on a large scale with parallel modules. Each module is a partially sunken 40 cm ca. 1×2 meter tub (inflatable children's pools). The photobioreactors are tethered to the sides of the tubs at water level with flexible cords, to allow waves to mix the algae. Wave generators having adjustable wave amplitude, wave frequency, and period are used, similar to FIG. 3. The wave generators are mounted in one module at short end, in one module along one side of the long side, in one module on both short sides, and in one module on both long ends. This allows generating all wave forms and measuring their damping over distance, with various types of synchrony and asynchrony to determine the most energy efficient ways of transferring carbon dioxide from the airspace to the algae containing medium. Algal photosynthesis is tested at various temperatures of the subtending water, knowing that the solubility of carbon dioxide decreases at higher temperatures. More sensitive pH measuring and wave actuating equipment is installed in these photobioreactors than that in Example 1 to decrease the periods between wave actuation, while keeping the number of waves approximately the same. This narrowing of pH span to (in most cases) pH 6.8-6.5 for on/off also facilitates better continuous suspension of the algae.

To the standard 0.5 mm slightly narrower plastic bottom are welded various plastic sheeting as top:
1. Standard non-toxic sheetings of various laminated plastics, with an anti-ultraviolet coating to protect the top plastic.
2. Similar plastics but specially designed to have a low beta value; i.e. pass oxygen preferentially over passing carbon dioxide.
3. Similar plastics but with an infrared reflective coating.
4. Similar plastics with diffusive (non-reflective) outer coatings that transmit low and early morning/late afternoon light to the algae.
5. Similar plastics with anti-droplet inner coatings, to prevent droplet formation that reflects incoming light.
6. Dust repellent plastics.
7. Combinations of the above.

In addition to the pH electrode in the medium (which basically measures carbon dioxide in the medium), oxygen and carbon dioxide measuring electrodes are inserted in the air space, allowing direct measure of photosynthesis. In this configuration, there was no continuous $CO_2$ input and gas phase bleeding as in Example 1, the supply is discontinuous based on the measurements.

An automatic sampling system removes samples at timed intervals and reads absorbancy at 650 and 735 nm, which measures algal growth, and an increase in the ratio 735/650 nm indicates microbial contamination and/or cell breakage.

Information from all the sensors/samples as well as on/off timing of the wave generators, together with incident light, temperature and algal density measures all go into a multi-channel data logger for further analysis, optimization during experimental runs, and future design considerations. Ultimately the results assist in deciding optimal harvest timing; daily or more than once during the day to best harvest solar energy. The sensor signals when the cultures have increased by the pre-programmed density increase, the oxygen vent is briefly closed and the harvest valve opened and a portion of the algae removed under the increased air-pressure, the vent reopened and an equal volume of fresh medium is introduced. The same harvesting technology is used in the further experiments.

While higher plants stop photosynthesis when air contains >30% oxygen, this is not so with algae cultivated at a high $CO_2$. It is necessary to ascertain the level of oxygen each species can withstand at high $CO_2$ before it is necessary to vent the airspace, and whether low beta plastics presently available will rapidly enough pass oxygen. This system allows optimizing parameters for when pure carbon dioxide is used (as from separation from natural gas before liquification to liquefied natural gas). Inputs of 4% $CO_2$ in air (similar to flue gas from natural gas burning plants) and a mixture of 14% $CO_2$, (6% oxygen, 80% nitrogen) representing purified flue gas from coal fired power plants are also tested, as this what is available at some locales.

No single plastic is optimal in all culture and economic situations. UV coatings lengthen the use life and increase the cost of the plastic. In cases where short half-life plastics are more economical or desirable for other reasons, then the added cost for UV protection is unwarranted. Where cooling is cheap and/or high temperature optimum algae or cyanobacteria are used, the partial concomitant loss of some photosynthetically active light and added cost with infrared reflecting plastics may be contra-indicated. Dust repellent plastics are unnecessary in areas of high rainfall but near imperative in dusty deserts. Thus, the results from the plastic study are applied for different locales.

Similarly, the results from different types of wave motion allow optimization for different species and growing systems. Larger size species require more mixing energy to remain suspended; high amplitude waves can cause light to hit open areas if the algal layer is too shallow; but the more shallow the layer the better the $CO_2$ diffusion and more dense the algal suspension that can be cultivated. The timing between the wave pulses and wave amplitude are experimentally determined to ascertain the optimal time and amplitude to set the wave generators such that near shear waves are generated that mix the algae layer. These near shear waves increase the gas-algae interface, facilitating efficient gas exchange between the air space and the algae growth medium, decreasing the amount of energy that needs to be expended to dissolve carbon dioxide from the air space to the media, and remove excess dissolved oxygen from the media.

Likewise, there is no single preferred depth of heat exchanging water beneath the photobioreactors for all uses. In areas with cool nights a greater depth is useful as sufficient heat from the day can be stored to keep the algae warm at night and require less cooling water during the day; algae that are warm at dawn begin active photosynthesis earlier during the day and can buffer the need for adding cooler water due to the cool nights. Also, the difference between the temperature of the water available for cooling and optimum temperature for algal growth (which is species specific and can be genetically modified) must be compared for deciding water depth.

The results indicate a considerable saving in capital costs (compressors, aerators, superstructure) over other closed systems, with the present bioreactor invention. There are even more projected savings in running costs; less sterilized medium, better cooling, less carbon dioxide wasted.

Example 3 Finned Bottom Photobioreactors

The photobioreactors in this example are identical to those in Example 2, except that flexible plastic fins are attached to the bottom plastic as described in FIGS. 4 and 5. The fins are wiggled by the waves such that they amplify the effect of the waves by wiggling or fluttering the bottom plastic of the photobioreactor. Different photobioreactor fin heights, lengths and distances between fins are checked, and the results costs as fabrication costs vs. energy saving, which will be different for different locations and different for different algal. The distance between the fins is experimentally determined to ascertain the optimal distances such that near shear waves are generated that mix the algae layer. These near shear waves that form increase the gas-algae interface, facilitating efficient gas exchange between the air space and the algae growth medium, lessening the amount of energy that needs to be expended to dissolve carbon dioxide from the air space to the media, and remove excess dissolved oxygen from the media.

The fins can be solid or hollow, and will have the added advantage of overcoming sag at the middle of the TLPBR due to the weight of the plastic, the algae, and the slight pressure inflicted by the minor pressure in the air-space. Using hollow fins adds to the buoyancy and to their strength.

Example 4: Wave Generation by Piezoelectric Activated Wires

Piezoelectric devices are amongst the most energy efficient manner of generating vibrations. Miniature vibrations in a thin layer of medium can be sufficient to execute the gas exchange of $CO_2$ from the air space to the medium. In this case wave motion is not needed and the subtending water will just serve as a temperature stabilizer and not a mechanical mixer as well.

Figure 6A:
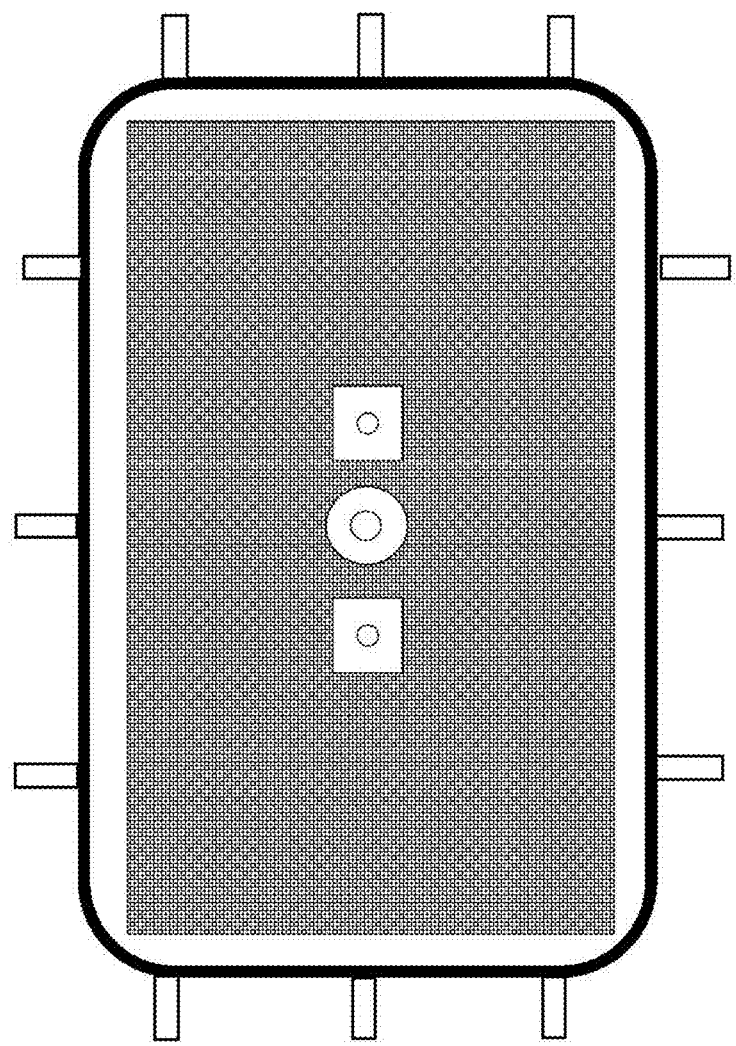
FIGS. 6A and B are a modified version of the photobioreactor shown in FIG. 3 whereby there is no wave generating machine. Instead wires are embedded in, or welded to the bottom of the TLPBR and mini-waves are generated by vibrating the wires by piezoelectric action. The wires can be stretched the width of the bioreactors (6B) or can be crisscrossed (6A) and actuated electronically in a manner calculated to form near shear waves.

Piezoelectric wires are embedded into the laminated bottom plastic at various distances during plastic sheet fabrication (FIG. 6A) or single transducers are embedded inside (FIG. 6B) or attached beneath the photobioreactor (not shown). Otherwise, the photobioreactor construction is the same as in Example 2. The algae are introduced into the photobioreactors as a dense suspension in a thin layer of 2.5-5 mm, except for a slightly sunken chamber made for the tip of the pH electrode. Experiments in these photobioreactors must be undergone for a long duration to ascertain the effect of the vibrations on the various plastics.

A similar long-term experiment is set up with the photobioreactor resting on piezoelectric wires and not embedded in the plastic. The wires are activated with different energies to vary the amplitude of the mini waves formed in the algal layer.

The wires can be stretched the width of the bioreactors and be held taut to prevent sag and keep the bioreactor level. Not all the vibrational energy will be expended in the thin layer of algae. Some of the vibrational energy will be expended in the subtending cooling water, and by doing so, facilitates heat exchange.

The results vary from alga to alga, with different layer thicknesses and energies optimal in different cases.

The value of this system will depend on the cost of large scale production of wire embedded plastic sheeting or the alternative external wires vs. the energy savings compared to waves, as well as the value of the cultivated algae. The timing of the pulses applied to the piezo-electric actuated wires or separate transducers is set such that they generate near shear waves that mix the algae layer. These near shear waves that form increase the gas-algae interface, facilitating efficient gas exchange between the air space and the algae growth medium.

Example 5 Wave Generation by Mini-Vibrators Attached to the Bottom Plastic

Mini-vibrators devices are highly energy efficient in generating vibrations. Miniature vibrations in a thin layer of medium can be sufficient to execute the gas exchange of $CO_2$ from the air space to the medium. In this case wave motion is not needed and the subtending water will just serve as a temperature stabilizer and not a mechanical mixer as well.

Figure 7:
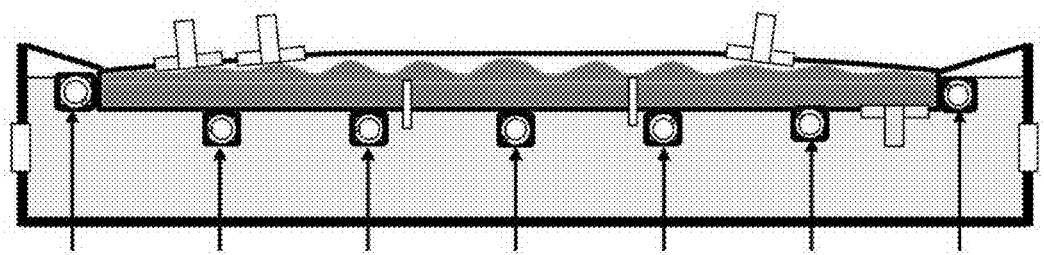
FIG. 7 is a modified version of the photobioreactor shown in FIG. 6 whereby there is no wave generating machine. Instead wires are attached to the bottom of the TLPBR and mini-waves are generated by low energy requiring, low DC voltage vibrators (see FIGS. 8A, B, C and D for details). The electrical wires providing the energy to the vibrators can be stretched the width of the bioreactors and be held taut to prevent sag and keep the bioreactor level.

The mini-vibrators and their electrical feedwires are embedded into the laminated bottom plastic at various distances during plastic sheet fabrication (FIG. 7), glued to the underside of the photobioreactors (FIG. 8A). Otherwise, the photobioreactor construction is the same as in Example 4. The algae are introduced into the photobioreactors at 2-4 times the density but to a thin layer of 2.5-5 mm, except that a slightly sunken chamber is made for the tip of the pH electrode. Experiments in these photobioreactors must be undergone for a long duration to ascertain the effect of the vibrations on the plastic.

Not all the vibrational energy will be expended in the thin layer of algae. Some of the vibrational energy will be expended in the subtending cooling water, and by doing so, facilitates heat exchange.

The results vary from algae to algae, with different layer thicknesses and energies optimal in different cases.

The value of this system will depend on the cost of large scale production of the vibrators and their wires embedded in the plastic sheeting vs. the energy savings compared to waves, as well as the value of the cultivated algae. The timing of a single mini-vibrator operation is set such that the traversing of a wave over it results in the intensification and rarefication of the algae layer by causing near shear waves. These near shear waves that form increase the gas-algae interface, facilitating efficient gas exchange between the air space and the algae growth medium. The process is detailed in FIG. 7 in which the device activation is timed when it is traversed by a sonic pulse wave and so does produce the near shear waves and turbulent vortices that promote gas-algae mixing.

Example 6 Wave Generation by Mini-Vibrators Attached in U-Shaped Plastic Profile Support Rods Mini-vibrators devices are highly energy efficient in generating vibrations. Miniature vibrations in a thin layer of medium can be sufficient to execute the gas exchange of $CO_2$ from the air space to the medium. In this case wave motion is not needed and the subtending water will just serve as a temperature stabilizer and not a mechanical mixer as well.

Figure 8B:
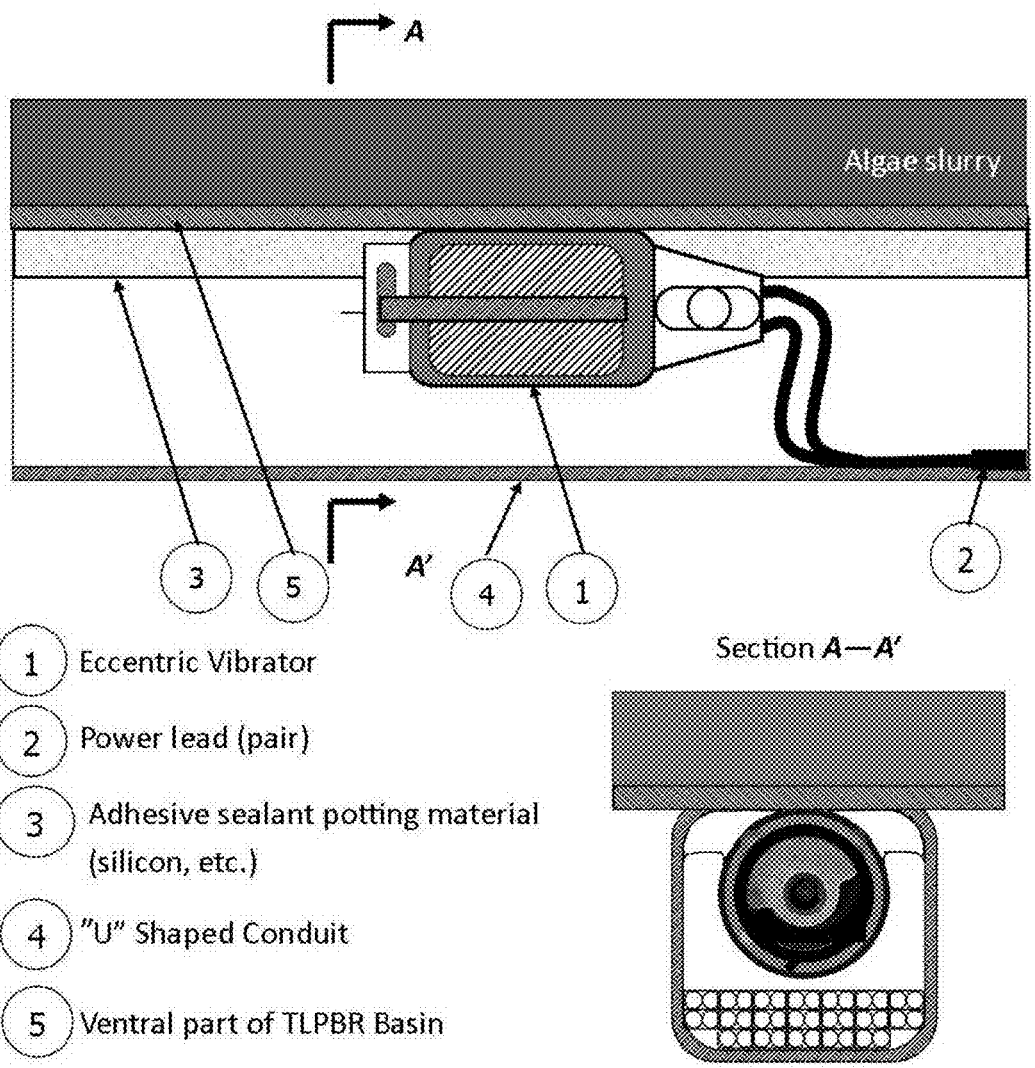
FIGS. 8A, B, C and D are different versions of the photobioreactor shown in FIG. 7 whereby waves are generated by mini-vibrator arrays, were the separate low energy requiring, low DC voltage vibrators are glued to the bottom (A) or embedded in U shaped plastic profiles where the space not occupied by the vibrators are filled with a hydrophobic plastic foam (e.g. polystyrene, or polyurethane) that confer buoyancy to the rigid structure (B). The vibrators can be pre-programmed to be excited at intervals that generate near shear waves (A and B) or hydrophones can be mounted nearby to detect wave motion and activate the vibrators to generate the near shear waves (C and D)
Figure 8C:
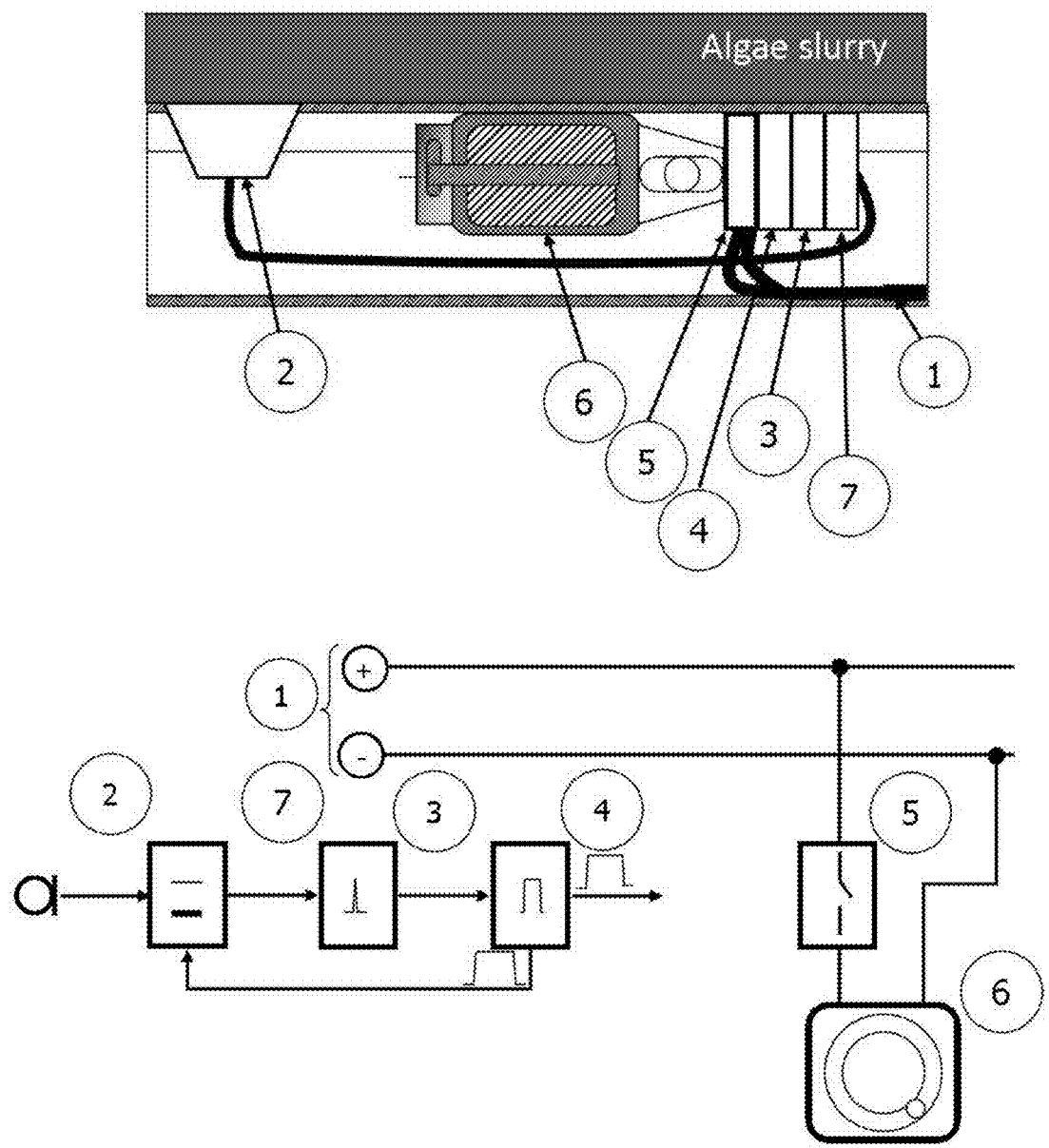

The mini-vibrators and their electrical feed wires are embedded into U shaped plastic profiles (similar to those used for external electrical conduits mounted on walls) with polystyrene filling the rest of the space in the profiles, such that the profiles are lighter than water. The profiles are mounted under the laminated bottom plastic at various distances, providing a leveling effect, preventing sag (FIG. 8B). Otherwise, the photobioreactor construction is the same as in Example 4. The algae are introduced into the photobioreactors at 2-4 times the density but to a thin layer of 2.5-5 mm, except that a slightly sunken chamber is made for the tip of the pH electrode. Experiments in these photobioreactors must be undergone for a long duration to ascertain the effect of the vibrations on the plastic. The timing and spacing of operation of adjacent mini-vibrators is either pre-set such that the traversing of a wave over them results in the intensification and rarefication of the algae layer by causing near shear waves (FIG. 8B), or hydrophones are mounted that provide the localized feedback to provide the same effect (FIGS. 8C and 8D). These near shear waves that form increase the gas-algae interface, and thus facilitate efficient gas exchange between the air space and the algae growth medium.

Not all the vibrational energy will be expended in the thin layer of algae. Some of the vibrational energy will be expended in the subtending cooling water, and by doing so, facilitates heat exchange.

The results vary from algae to algae, with different layer thicknesses and energies optimal in different cases.

The value of this system will depend on the cost of large scale production of the vibrators and their wires embedded in the plastic sheeting vs. the energy savings compared to waves, as well as the value of the cultivated algae.

An estimation of the relative cost advantage over other photobioreactor configurations for a one hectare (see Table 5 below) and 100 hectare (see Table 6 below) facilities clearly show the economic superiority of the system.

TABLE 5

Unit biomass production costs for ponds and photobioreactors for 1 Ha

| Base case - Netherlands | Raceway | Tubulars | Flat panels | Present floating |
|---|---|---|---|---|
| | Eurocents/kg DW algae as paste | | | |
| Major equipment + power | | | | |
| PVC liner | 49.33 | | | |
| Centrifuge[a]/flocculation[b] | 118.66[a] | 43.26[a] | 38.61[a] | 2.00[b] |
| Power | 17.02[a] | 3.65[a] | 2.54[a] | 1.00[b] |
| Medium preparation | 81.31 | 29.29 | 19.31 | 1.00 |
| Power | 3.80 | 0.84 | 0.64 | 0.02 |
| Harvest buffer tank | 25.11 | 6.28 | 4.09 | 0.02 |
| Culture circulation pump | | 73.74 | | Harvest 2.00 |
| Power | | 47.06 | | 2.00 |
| Steel framework | | | 11.73 | — |
| Blower/paddle wheel | 4.52 | 6.91 | 73.55 | Vibrators 0.16 |
| Power | 3.17 | 5.83 | 240.67 | 4.50 |
| Other capital | | | | |
| Installation costs | 41.84 | 47.84 | 44.19 | 44.00 |
| Instrumentation costs | 27.89 | 15.95 | 14.73 | 15.00 |
| Piping | 83.68 | 47.84 | 44.19 | 2.20 |
| Buildings | 83.68 | 47.84 | 44.19 | 44.00 |
| Variable costs (ex. power) | | | | |
| Polyethylene tubing/sheet | | 12.76 | 9.76 | 10.00 |
| Culture medium | 44.00 | 44.00 | 44.00 | 8.00 |
| Carbon dioxide | 33.67 | 33.67 | 33.67 | 16.00 |
| Medium filters | 44.42 | 18.39 | 13.88 | 2.00 |
| Labor | 579.55 | 289.78 | 188.58 | 200.00 |
| Salary overhead | 144.89 | 72.44 | 47.15 | 50.00 |
| Maintenance | 42.91 | 49.07 | 45.32 | 45.00 |
| General plant overheads | 342.35 | 93.39 | 128.65 | 100.00 |
| Sum | 1772.00 | 990.00 | 1049.00 | 549.26 |

Data for raceway, tubular and flat plate photobioreactors from N. H. Norsker et al. Biotechnology Advances 29 (2011) 24-27

TABLE 6

Unit biomass production costs for ponds and photobioreactors covering 100 Ha

| Base case - Netherlands | Raceway | Tubulars | Flat panels | Present floating |
|---|---|---|---|---|
| | Eurocents/kg DW algae as paste | | | |
| Major equipment + power | | | | |
| PVC liner | 40.45 | | | |
| Centrifuge[a]/flocculation[b] | 44.45[a] | 9.54[a] | 7.23[a] | 2.00[b] |
| Power | 19.12 | 3.96 | 2.99 | 1.00 |
| Medium preparation | 44.66 | 9.29 | 7.01 | 1.00 |
| Power | 4.20 | 0.81 | 0.61 | 0.02 |
| Harvest buffer tank | 18.84 | 3.89 | 2.94 | 1.80 |
| Culture circulation pump | | 73.33 | | 2.00 |
| Power | | 47.06 | | 2.00 |
| Steel framework | | | 11.73 | |
| Blower/paddle wheel | 4.53 | 0.99 | 69.30 | Vibrators 0.16 |
| Power | 3.18 | 5.89 | 240.67 | 4.50 |
| Other capital | | | | |
| Installation costs | 22.94 | 29.11 | 29.46 | 30.00 |
| Instrumentation costs | 15.29 | 9.70 | 9.82 | 10.00 |
| Piping | 45.88 | 29.11 | 29.46 | 2.00 |
| Buildings | 45.88 | 29.11 | 29.46 | 30.00 |
| Variable costs (ex. power) | | | | |
| Polyethylene tubing/sheet | | 12.76 | 9.76 | 10.00 |
| Culture medium | 44.00 | 44.00 | 44.00 | 6.00 |
| Carbon dioxide | 33.67 | 33.67 | 33.67 | 10.00 |
| Medium filters | 44.42 | 18.39 | 13.88 | 2.00 |
| Labor | 12.56 | 6.38 | 4.09 | 3.00 |
| Salary overhead | 3.14 | 1.57 | 1.02 | 0.75 |
| Maintenance | 23.63 | 29.86 | 30.22 | 30.00 |
| General plant overheads | 19.85 | 17.09 | 18.87 | 25.00 |
| Sum | 495.00 | 415.00 | 596.00 | 173.00 |

Data for raceway, tubular and flat plate photobioreactors from N. H. Norsker et al. Biotechnology Advances 29 (2011) 24-27

Because the base economic data were from a temperate climate, where it is less likely that algae will be commercially cultivated, a sensitivity analysis was made comparing with a more tropical setting in Table 7. The economic advantage of the present system is even more pronounced from this analysis.

TABLE 7

Sensitivity analysis. Biomass cost with different scenarios (100 ha facility)

| Scenario | Raceway | Tubulars | Flat panels | present floating |
|---|---|---|---|---|
| | (€/kg DW) | | | |
| 1. Netherlands (base case) | 4.95 | 4.16 | 5.96 | 1.73 |
| 2. Tropics (Bonaire) | 2.83 | 2.44 | 3.26 | 0.95 |
| 3. Minimum mixing | | 3.06 | 3.08 | 0.95 |
| 4. No-cost $CO_2$ + min. mixing | 4.61 | 2.72 | 2.74 | 0.85 |
| 5. Incr. photosynthetic efficiency + 4 above | 3.06 | 1.83 | 1.88 | 0.85 |
| 6. In tropics + 5 above | 1.63 | 1.14 | 1.12 | 0.67 |

Data for raceway, tubular and flat plate photobioreactors from N. H. Norsker et al. Biotechnology Advances 29 (2011) 24-27

Example 7—Preventing Photobioreactor Sag with Buoyant Subtending Enclosed Bubbles An additional method of preventing the sag caused by the slight positive air pressure used to create the air space as well as by the weight of mini-vibrators or piezo electrically activated wires, as an alternative to the rigid fins (Example 3) or rigid profiles (Example 6) is to attach strips of bubbled plastic sheeting at appropriate intervals on the underside of the lower sheet. These are attached such that the distances are sufficient to maintain a near level surface for algal cultivation in the photobioreactor, but sufficiently apart so as not to overly impede heat exchange with the subtending water (FIG. 9).

Example 8: Wave Generation by Vibratory Rocking of a Rigid-Bottom

Figure 10:
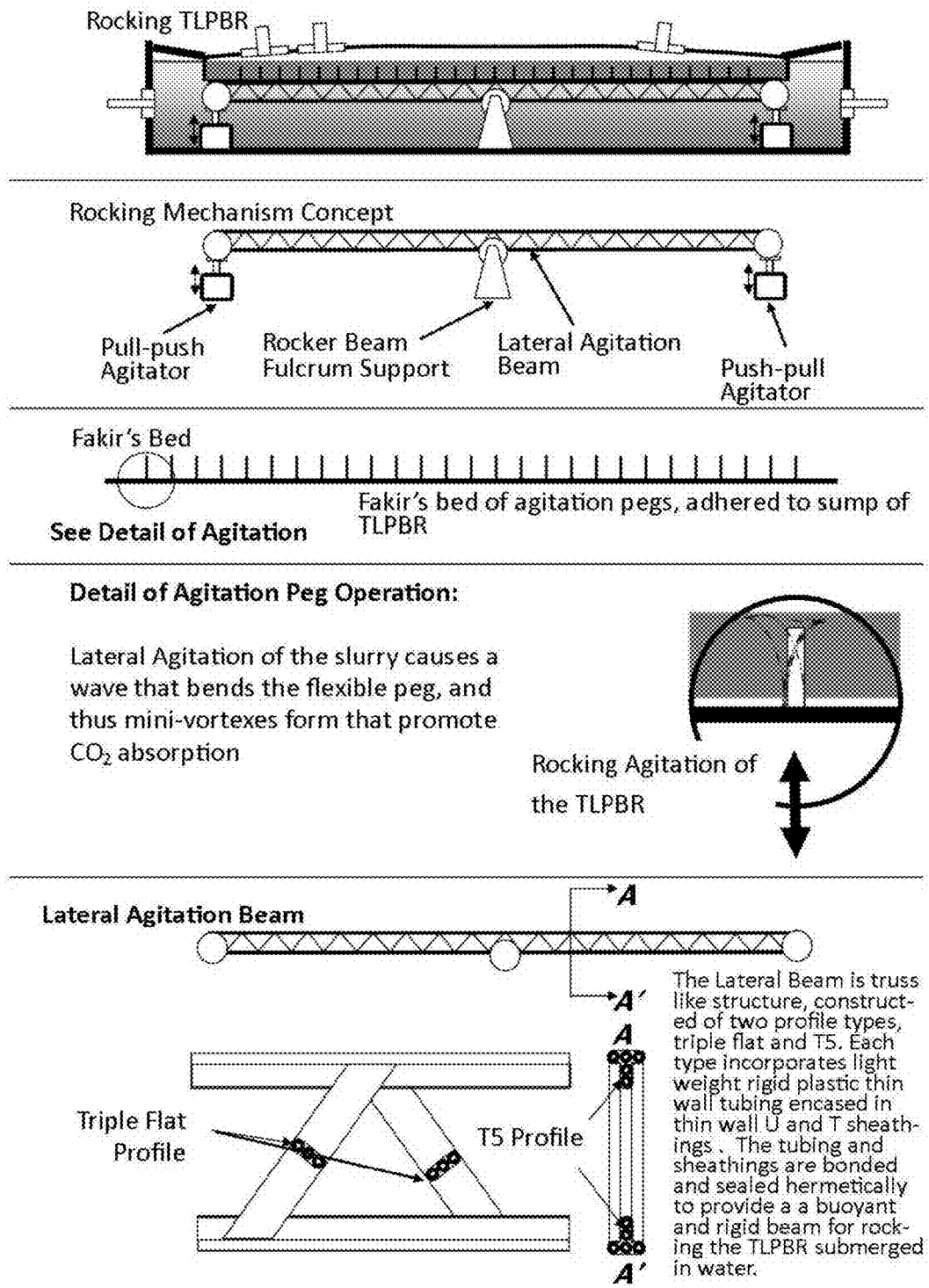
FIG. 10 is an illustration of a solid, bottom floating photobioreactor where waves are generated by low amplitude vibratory motion. Because it is floating, there is very little weight bearing, allowing need for lighter supports and minimal energy to perform the vibratory, wave-generating rocking.

An alternative to the very efficient transducer or mini-vibrator induced waves to promote algae-gas mixing, which is less dependent upon complex electronic controls is by vibratory rocking of a rigid bottom photobioreactor. Such rocking chemical solutions areis a known process in photographic plate processing and development. Its application to large scale algae gas mixing in a thin film bioreactor is novel. The increase area in the between the $CO_2$ gas and the alga slurry caused by the traversing wave should allow more gas to be absorbed by the algae. This configuration is realizable by making the photobioreactor structure more rigid with a truss like structure, supporting the truss structure at its center to form a fulcrum and installing counter moving actuators at the ends of the truss. Enhancement of the gas-algae interface within the photobioreactor is achieved by vertical flexible pegs resembling a fakir's bed in the photobioreactor sump. The amplitude range of the rocking at the photobioreactor ends is about twice the thickness of the algae slurry layer. The rocking frequency is set to promote a wave that dampens considerably when it reaches the opposite side so as not to form a standing wave or waves in the slurry. The truss that traverses the ventral side of the photobioreactor basin is made of rigid plastic tubing enclosed in U shaped channels which are then fashioned into the truss beam, or by using 1-3 mm thick sheets plastic (e.g. recycled polycarbonate) with molded ridges to enhance rigidity. The rocking configuration is described schematically in FIG. 10.

Although the above examples and following descriptions may be directed to one or more certain configurations of thin layer photobioreactor, it should be understood that the present subject matter is not limited to any specific configuration and may be used in various reactors having various geometric shapes that can support or create a thin layer of microalgae floating on a cooling solution, with carbon dioxide mixed into the medium by wave motion, without the need for bubbling of carbon dioxide. Floatation is maintained by having an air space above the algae, and leveling on the cooling water by taut horizontal wires across the bioreactors and/or attached plastic bubbles in rows the length of the photobioreactor. Production scale photobioreactors can be 3-20 meters but preferably 4-5 meters in width and 5-500 meters or longer (but preferably 15-250) meters in length, constructed from welded plastic sheets with bottom and top sheets having different properties, with spaced grommets welded at fixed intervals for flexible tethering to the sides, and ports inserted for control instrumentation and for introducing media and harvesting.

In most embodiments the feed of carbon dioxide to the "air space" is either pure carbon dioxide (e.g. separated from natural gas prior to liquification of the natural gas), which is the preferred source, or detoxified flue gas from coal or gas-fired power generation or other industrial sources containing ca. 4-14% carbon dioxide. Purification is routinely required to remove sulfur compounds, phytotoxic heavy metals, and in some cases hydrocarbons or organic molecules.

In the preferred embodiments, the carbon dioxide is mixed by using subtending wave motion generated by a wave machine similar in concept to those used to generate waves in swimming pools (but that generate waves of much lower amplitude) or by piezoelectric operated vibrating wires embedded at fixed distances in or on the lower layer of plastic, by small vibrators attached on the underside of the lower plastic, or by natural wave motion. The wave motion can be augmented by fluttering fins mounted on the underside of the plastic at right angles to the wave motion. The nano piezoelectric wire configuration is used as a power transducer to convert electrical energy into mechanical energy. The hard wiring of piezoelectric elements as nano size strands are attached or embedded as an array of orthogonally placed wires forming a grid. By sequentially applying voltages to each submerged piezoelectric wire wave motions are produced whereby the nodes and antinodes (crest and troughs) of the resulting waves have different wavelengths and positions. The dimensions and frequency of the surface waves are varied by varying the sequence of the electrical power signals applied to each piezoelectric wire strand to ascertain the most energy efficient introduction of carbon dioxide from the airspace into the culture medium without damage to the algae. Since strands are orthogonally oriented (i.e. grid like), varying the electric power application sequence to the strands ripples, peaked columns resembling a histogram, eddies, whirlpools, etc, are created. The waves are generated for durations and frequencies such that $CO_2$ brings the pH of the growth medium to pH 6.5-7.5 the optimum range of most algae or cyanobacteria (or to other pH ranges for organisms with other pH optima) by $CO_2$ dissolution in the medium from the airspace, as it was demonstrated that the potential rate of photosynthesis is too fast for simple diffusion from the airspace to be sufficient, even at layers of 3-5 mm thickness.

In one embodiment the electrical power to supply the mixing can come directly from photovoltaic panels with minimum battery storage needed, as the both the rate of photosynthetically utilized $CO_2$ (and thus need for wave facilitated mixing) and the rate photovoltaic power generation are both dependent solar intensity and thus there will be the greatest power available at peak need time, to supply energy to the DC operating wave generators and medium metering pumps.

In the embodiments where waves are artificially generated, the timing and amplitude of the wave pulses can be set such that they generate near shear waves that mix the algae layer. These near shear waves that form increase the gas-algae interface, facilitating efficient gas exchange between the air space and the algae growth medium.

Where natural wave motion is used, the tether lines are tightened or loosened to achieve the same mixing effect. Because there is minimal gas flow out of the system (unlike in photobioreactors with continuous gap bubbling, or "plugs" of waves for movement and venting), there is little loss of water due to evaporation and far less need for adding fresh water to offset salinization.

In the on-land embodiments of the technology, the rate of flow of the subtending water is controlled to maintain an optimal (cost-effective) temperature for the algae. The depth of water will vary from climate to climate; with deeper water being used where day/night temperature fluctuations are the greatest; to store heat to keep the algae warmer at night and at optimal photosynthetic temperature from early morning, moving and replacing the least amount of water necessary. When the body of water is a reservoir for drinking water or irrigation, the presence of bioreactors lowers evaporative loss of water, and the lack of light prevents algae and cyanobacteria from proliferating and producing toxins and other undesirable metabolites.

The invention claimed is:
1. A photobioreactor for cultivating and growing microalgae comprising:
(i) a sealed thin, visible light conducting flexible plastic sheeting comprising an upper plastic sheeting panel and a lower plastic sheeting panel, the upper plastic sheeting panel and the lower plastic sheeting panel collectively forming a sealed tubular flat container, whereby one face of the lower plastic sheeting panel floats on the surface of a temperature modulating body of water and wherein the other face of the lower plastic sheeting panel is coated with microalgae within an aqueous medium forming a thin aqueous microalgae layer that is less than 1 cm in thickness; and where said upper plastic sheeting panel is held above the thin aqueous microalgae layer due to the slightly inflated airspace, which also supplies buoyancy to the system;
(ii) the space between a top surface of said thin aqueous microalgae layer and an interior surface of said upper plastic sheeting panel forms a gas space and is maintained at predetermined ratios of carbon dioxide to oxygen;
(iii) a source of light;
(iv) a vibration generating system assembled to said lower plastic sheeting panel, said vibration generating system comprising more than one vibration generating element arranged to generate near shear waves at the point where waves from each pulse from the respective vibration generating element meet, said vibration generating system oscillates said lower plastic sheeting panel causing oscillation of said thin aqueous microalgae layer; wherein said near shear waves are generated to one of directly or indirectly agitating the thin aqueous microalgae layer, thus increasing an exposure of said microalgae within said thin aqueous microalgae layer to the gas phase, facilitating carbon dioxide absorption;
(v) a gas pressure generating system for increasing the partial gas pressure of the gas space;
(vi) a device adapted to agitate the body of water and the microalgae layer in the bioreactor, wherein the agitation facilitates a gaseous exchange between the microalgae layer and the air space, wherein the gaseous exchange does not require bubbling, and
(vii) inlet and outlet openings.
2. A process for cultivating and growing microalgae comprising the process comprising steps of:
(a) providing a photobioreactor comprising:
(i) a sealed thin, visible light conducting flexible plastic sheeting comprising an upper plastic sheeting panel and a lower plastic sheeting panel, the upper plastic sheeting panel and the lower plastic sheeting panel collectively forming a sealed tubular flat container, whereby one face of the lower plastic sheeting panel floats on the surface of a temperature modulating body of water and where said upper plastic sheeting panel is held above the other face of the lower plastic sheeting panel due to the slightly inflated air space, wherein the other slightly inflated air space also supplies buoyancy to the system;
(ii) the air space between a top surface of said other face of the lower plastic sheeting panel and an interior surface of said upper plastic sheeting panel forms a gas space and is maintained at predetermined ratios of carbon dioxide to oxygen;
(iii) a source of light;
(iv) a vibration generating system assembled to said lower plastic sheeting panel said vibration generating system comprising more than one vibration generating element arranged to generate near shear waves at the point where waves from each pulse from the respective vibration generating element meet;
(v) a gas pressure generating system in fluid communication with the gas space;
(vi) an agitation device, and
(vii) inlet and outlet openings;
(b) coating the other face of the lower plastic sheeting panel with a microalgae within an aqueous medium forming a thin aqueous microalgae layer that is less than 1 cm in thickness;
(c) floating the first face of the plastic sheeting on the surface of a body of heat exchanging water;
(d) agitating the plastic sheeting using the more than one vibration generating element, causing vibrations thereby generating a wave-like motion in said microalgae layer, wherein the agitation creates said near shear waves;
(e) facilitating dissolution of the carbon dioxide from the gas space into the microalgae layer by increasing a pressure within the gas space;
(f) exposing the aqueous microalgae layer to light through said upper plastic sheeting panel, which is held above the aqueous microalgae layer by the slightly inflated air space;
(g) facilitating a gaseous exchange between the aqueous microalgae layer and the air space by combining exposure of the aqueous microalgae layer to the pressurized gas in the air space and circulating the aqueous microalgae layer using the near shear waves, wherein the process does not require bubbling;
(h) replenishing said aqueous medium through an opening into the system, thereby forcing a portion of said microalgae of said aqueous microalgae layer out of the photobioreactor through said outlet due to the flow of said aqueous medium and the gas pressure exerted in the photobioreactor, and thus facilitating harvesting of microalgae through said outlet.
3. The photobioreactor according to claim 1, wherein said microalgae include at least one of algae, cyanobacteria, and small aquatic plants selected from *Phaeodactylum tricornutum, Amphiprora hyaline, Amphora* spp., *Chaetoceros muelleri, Navicula saprophila, Nitzschia* spp., *Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleoabundans, Synechococcus elongatus* PCC 6301, *Botryococcus braunii, Gloeobacter violaceus* PCC 742, *Synechococcus* PCC 7002, *Synechococcus* PCC 7942, *Synechocystis* PCC 6803, *Thermosynechococcus elongatus* BP-1, *Nannochloropsis oculata, Nannochloropsis salina, Nannochloropsis* spp., *Nannochloropsis gaditana, Isochrysis* aff. *galbana, Aphanocapsa* sp., *Botryococcus sudeticus, Euglena gracilis, Nitzschia palea, Pleurochrysis carterae, Tetraselmis chuii, Pavlova* spp., and *Nannochloris* spp. as representatives of all algae and cyanobacteria species, as well as small floating plants from the duckweed family (Lemnaceae).
4. The photobioreactor according to claim 1, wherein wave amplifying fins are attached beneath said one face of the lower plastic sheeting.

5. The photobioreactor according to claim 1, wherein the thickness of the microalgae coating is in the range of 2.5 to 5.0 mm.

6. The photobioreactor according to claim 1, wherein a culture medium is maintained at a predetermined pH for each algal species by controlling an amount of acidifying dissolved carbon dioxide by regulating the system generating near shear waves.

7. The photobioreactor according to claim 1, wherein the temperature of the body of water is maintained at a predetermined temperature for each algal species through the use of heat exchange with the subtending water upon which the photobioreactor floats.

8. The photobioreactor according to claim 1, wherein said exposure is to one of sunlight, or sunlight augmented with artificial illumination, or artificial illumination.

9. The photobioreactor according to claim 1, wherein the vibration generating system further comprises piezoelectric wires.

10. The photobioreactor according to claim 1, wherein the vibration generating system further comprises low amplitude mechanical wave machines that are one of embedded in or bonded to said one face of the lower plastic sheeting panel.

11. The photobioreactor according to claim 2, wherein said algal medium agitation is generated by mini-vibrators resulting in near shear waves in the aqueous medium.

12. The photobioreactor according to claim 2, wherein said algal medium agitation is generated by hydrophonic-generated acoustic pulses resulting in near shear waves in the aqueous medium.

13. The photobioreactor according to claim 3, wherein said algae is at least one of: freshwater *Chlorella* spp., *Chlamydomonas reinhardtii; Synechococcus* PCC 7002 (marine), *Synechococcus* 7942 (freshwater), marine *Nannochloris* spp., *Nannochloropsis* spp., *Isochrysis* sp. CS-177, *Pavlova lutheri; Phaeodactylum tricornutum*, and *Tetraselmis chui*.

14. The photobioreactor according to claim 1, wherein said thin, visible light conducting flexible plastic sheeting is fabricated including at least one of the following polymers: polyethylene, polypropylene, polybutylene, polyester, polycarbonate, polyamide, polyvinyl chloride, polyvinylidene chloride, polystyrene, copolymers of butadiene and styrene, polyurethane, polyacrylonitrile, polyacrylate, copolymers, mixed laminations, and combinations thereof said polymers, and one of:
blended with plasticizers, minerals, pesticides and anti oxidants, or
excluding plasticizers, minerals, pesticides and anti oxidants.

15. The photobioreactor according to claim 1, wherein said sheeting panel is fabricated of a material which limits evaporation from and production of algal and cyanobacterial toxins in said reservoirs.

16. The photobioreactor of claim 1, wherein the visible light conducting flexible plastic sheeting is characterized by a low beta value having a much higher permeability to oxygen than carbon dioxide.

17. A process according to claim 2, wherein said photobioreactor is suitable for culturing small water plants including Lemnaceae.

18. The photobioreactor according to claim 2, wherein said microalgae are algae and cyanobacteria selected from *Phaeodactylum tricornutum, Amphiprora hyaline, Amphora* spp., *Chaetoceros muelleri, Navicula saprophila, Nitzschia* spp., *Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleoabundans, Synechococcus elongatus* PCC 6301, *Botryococcus braunii, Gloeobacter violaceus* PCC 742, *Synechococcus* PCC 7002, *Synechococcus* PCC 7942, *Synechocystis* PCC 6803, *Thermosynechococcus elongatus* BP-1, *Nannochloropsis oculata, Nannochloropsis salina, Nannochloropsis* spp., *Nannochloropsis gaditana, Isochrysis* aff. *galbana, Aphanocapsa* sp., *Botryococcus sudeticus, Euglena gracilis, Nitzschia palea, Pleurochrysis carterae, Tetraselmis chui, Pavlova* spp. and *Nannochloris* spp. as representatives of all algae and cyanobacteria species.

19. The photobioreactor according to claim 2, wherein wave amplifying fins are attached beneath the lower plastic sheeting panel.

20. The photobioreactor according to claim 2, wherein the thickness of the microalgae coating is in a range of 2.5 to 5.0 mm.

21. The photobioreactor according to claim 2, wherein a culture medium is maintained at a predetermined pH for each algal species by control of the near shear wave mixing allowing acidification by increasing dissolved carbon dioxide.

22. The photobioreactor according to claim 2, wherein the temperature of the body of water is maintained at a predetermined temperature for each algal species through the use of heat exchange with the subtending water upon which the photobioreactor floats.

23. The photobioreactor according to claim 2, wherein said exposure is to one of sunlight, or sunlight augmented with artificial illumination, or artificial illumination.

24. The photobioreactor according to claim 2, wherein the vibration generating system further comprises piezoelectric wires.

25. The photobioreactor according to claim 2, wherein the vibration generating system further comprises low amplitude mechanical wave machines that are one of embedded in or bonded to said one face of the lower plastic sheeting panel.

26. The photobioreactor according to claim 2, wherein said sheeting is based upon at least one of the following polymers: polyethylene, polypropylene, polybutylene, polyester, polycarbonate, polyamide, polyvinyl chloride, polyvinylidene chloride, polystyrene, copolymers of butadiene and styrene, polyurethane, polyacrylonitrile, polyacrylate, copolymers, mixed laminations, and combinations thereof said polymers, and one of:
blended with plasticizers, minerals, pesticides and anti oxidants, or
excluding plasticizers, minerals, pesticides and anti oxidants.

27. The photobioreactor according to claim 2, wherein said sheeting can be used to cover reservoirs, thus limiting evaporation and limiting production of algal and cyanobacterial toxins in the reservoirs.

28. The photobioreactor according to claim 2, wherein the plastic sheeting is characterized by a low beta value having a much higher permeability to oxygen than carbon dioxide.

* * * * *